United States Patent
Miyazaki

(10) Patent No.: US 9,993,524 B2
(45) Date of Patent: Jun. 12, 2018

(54) PROPHYLACTIC OR THERAPEUTIC AGENT FOR HEPATIC DISEASES

(71) Applicant: Toru Miyazaki, Tokyo (JP)

(72) Inventor: Toru Miyazaki, Tokyo (JP)

(*) Notice: Subject to any disclaimer, the term of this patent is extended or adjusted under 35 U.S.C. 154(b) by 27 days.

(21) Appl. No.: 14/396,569

(22) PCT Filed: Apr. 26, 2013

(86) PCT No.: PCT/JP2013/062469
§ 371 (c)(1),
(2) Date: Oct. 23, 2014

(87) PCT Pub. No.: WO2013/162021
PCT Pub. Date: Oct. 31, 2013

(65) Prior Publication Data
US 2015/0094268 A1 Apr. 2, 2015

(30) Foreign Application Priority Data
Apr. 27, 2012 (JP) .................. 2012-103958

(51) Int. Cl.
| | |
|---|---|
| *A61K 38/00* | (2006.01) |
| *A61K 45/00* | (2006.01) |
| *A61K 31/713* | (2006.01) |
| *A61P 1/16* | (2006.01) |
| *A61P 35/00* | (2006.01) |
| *C12N 15/09* | (2006.01) |
| *G01N 33/15* | (2006.01) |
| *G01N 33/68* | (2006.01) |
| *G01N 33/50* | (2006.01) |
| *A61K 38/17* | (2006.01) |
| *G01N 33/574* | (2006.01) |
| *A61K 49/00* | (2006.01) |
| *C07K 14/47* | (2006.01) |

(52) U.S. Cl.
CPC ........ *A61K 38/1761* (2013.01); *A61K 31/713* (2013.01); *A61K 45/00* (2013.01); *A61K 49/0004* (2013.01); *A61K 49/0008* (2013.01); *C07K 14/4747* (2013.01); *G01N 33/5088* (2013.01); *G01N 33/57438* (2013.01); *G01N 33/6893* (2013.01); *A61K 38/00* (2013.01); *G01N 2800/085* (2013.01)

(58) Field of Classification Search
None
See application file for complete search history.

(56) References Cited

U.S. PATENT DOCUMENTS

| | | | |
|---|---|---|---|
| 2010/0331244 A1 | 12/2010 | Miyazaki | |
| 2013/0115220 A1 | 5/2013 | Miyazaki | |

FOREIGN PATENT DOCUMENTS

WO    WO 2011/145723 A1    11/2011

OTHER PUBLICATIONS

Merck Manual, "Alcoholic Liver Disease", at URL merckmanuals.com/home/liver_and_gallbladder_disorders/alcoholic_liver_disease/alcoholic_liver_disease.html accessed Feb. 26, 2015.*
Merck Manual, "overview of hepatitis", at URL merckmanuals.com/home/liver_and_gallbladder_disorders/hepatitis/overview_of_hepatitis.html?qt=hepatitis&alt=sh accessed Feb. 26, 2015.*
Merck Manual, "cirrhosis of the liver", at URL merckmanuals.com/home/liver_and_gallbladder_disorders/fibrosis_and_cirrhosis_of_the_liver/cirrhosis_of_the_liver.html?qt=cirrhosis&alt=sh accessed Feb. 26, 2015.*
Merck Manual, "primary liver cancers", at URL merckmanuals.com/home/liver_and_gallbladder_disorders/tumors_of_the_liver/primary_liver_cancers.html?qt=livercancers&alt=sh accessed Feb. 26, 2015.*
Merck Manual, "metastatic liver cancer", at URL www.merckmanuals.com/home/liver_and_gallbladder_disorders/tumors_of_the_liver/metastatic_liver_cancer.html accessed Feb. 26, 2015.*
Merck Manual, "overview of blood vessel disorders of the liver", at URL  merckmanuals.com/home/liver_and_gallbladder_disorders/blood_vessel_disorders_of_the_liver/overview_of_blood_vessel_disorders_of_the_liver.html accessed Feb. 26, 2015.*
Merck Manual, "cholestasis," at URL www.merckmanuals.com/home/liver_and_gallbladder_disorders/manifestations_of_liver_disease/cholestasis.html accessed Feb. 26, 2015.*
Merck Manual, "fatty liver," at URL merckmanuals.com/home/liver_and_gallbladder_disorders/manifestations_of_liver_disease/fatty_liver.html accessed Feb. 26, 2015.*
Yamazaki et al., "Circulating AIM as an indicator of liver damage and hepatocellular carcinoma in humans," PLOS one 9:1-12 (2014).*
Mera et al., "Serum levels of apoptosis inhibitor of macrophage are associated with hepatic fibrosis in patients with chronic hepatitis C," BMC Gastroenterol. 14:1-10 (2014).*
Gray et al., "A proteomic strategy to identify novel serum biomarkers for liver cirrhosis and hepatocellular cancer in individuals with fatty liver disease," BMC Cancer 9:1-11 (2009).*
De Jong et al., "Of Mice and Humans: Are They the Same?—Implications in Cancer Translational Research," J Nucl Med 51:501-504 (2010).*
Arai et al.; A Role for the Apoptosis Inhibitory Factor AIM/Spα/Api6 in Atherosclerosis Development; Cell Metabolism, vol. 1, Mar. 2005, pp. 201-213.
Haruta et al.; Association of AIM, a Novel Apoptosis Inhibitory Factor, with Hepatitis via Supporting Macrophage Survival and Enhancing Phagocytotic Function of Macrophages; Journal of Biological Chemistry, vol. 276, No. 25, Jun. 22, 2001, pp. 22910-22914.
Kurokawa et al.; Apoptosis Inhibitor of Macrophage (AIM) is Required for Obesity-Associated Recruitment of Inflammatory Macrophages into Adipose Tissue; PNAS, vol. 108, No. 29, Jul. 19, 2011, pp. 12072-12077.

(Continued)

*Primary Examiner* — Julie Ha
*Assistant Examiner* — Kristina M Hellman
(74) *Attorney, Agent, or Firm* — Morgan, Lewis & Bockius LLP

(57) ABSTRACT

The present disclosure provides a prophylactic or therapeutic agent for a hepatic disease, containing AIM or a partial peptide thereof, or a nucleic acid containing a base sequence encoding the same. The present discloses also provides a method of screening for a prophylactic or therapeutic agent for a hepatic disease, comprising using an animal obtained by loading a non-human mammal deficient in AIM expression with a high fat diet and the like.

10 Claims, 8 Drawing Sheets

(56) References Cited

OTHER PUBLICATIONS

Kurokawa et al.; Macrophage-Derived AIM is Endocytosed into Adipocytes and Decreases Lipid Droplets via Inhibition of Fatty Acid Synthase Activity; Cell Metabolism, 11, Jun. 9, 2010, pp. 479-492.

Kuwata et al.; AIM Inhibits Apoptosis of T Cells and NKT Cells in Corynebacterium-Induced Granuloma Formation in Mice; American Journal of Pathology, vol. 162, No. 3, Mar. 2003, pp. 837-847.

Lu et al.; Peroxiredoxin 2:A Potential Biomarker for Early Diagnosis of Hepatitis B Virus Related Liver Fibrosis Identified by Proteomic Analysis of the Plasma; BMC Gastroenterology, 10:115, 2010, 13 pages.

Miyazaki; Aiming at Development of New Treatment Method of Arteriosclerosis by Functional Control of Apoptosis Inhibitory Factor AIM; Therapeutic Research, vol. 29, No. 2, Symposium: Arteriosclerosis Update 2007, 2008, pp. 144-151 along with English translation of same.

Miyazaki et al.; Increased Susceptibility of Thymocytes to Apoptosis in Mice Lacking AIM, A Novel Murine Macrophage-derived Soluble Factor Belonging to the Scavenger Receptor Cysteine-rich Domain Superfamily; J. Exp. Med., vol. 189, No. 2, Jan. 18, 1999, pp. 413-422.

Stepanova et al.; Protein Pathway Biomarker Signature Associated with Superimposed Non-alcoholic Steatohepatitis (NASH) and Advanced Fibrosis in Patients with Chronic Hepatitis C; Journal of Hepatology, vol. 52, 2010 (abstract only) pp. 5157.

International Search Report for PCT/JP2013/062469 dated Jul. 23, 2013.

Teramoto, Obesity and Fatty Liver, Progress in Japanese Medicine, 16: 440-442, (1995).

First Office Action with Search Report issued in corresponding Chinese Patent Application No. 201380022312.6 dated Aug. 31, 2015.

Angulo (2002) Nonalcoholic Fatty Liver Disease, N. Engl. J. Med. 346:1221-1231.

Teramoto (1995) Obesity and Fatty Liver, Progress in Japanese Medicine, 16:440-442 (English Translation, pp. 1-6).

Haruta et al., "Intrahepatic biliary epithelial cell damage and inflammation in portal tract in association with chronic colitis-harboring TCRalpha -/- mice," Hepatology Research, 34: 3-8 (2006).

Haruta et al., "Alleviation of Lipopolysaccharide-Induced Acute Liver Injury in Propionibacterium Acnes-Primed AIM (Apoptosis Inhibitor Expressed by Macrophages) Deficient Mice," Hepatology, 32: 177A (2000).

Supplementary European Search Report for EP 13 78 1041 dated Apr. 14, 2016.

* cited by examiner

HE staining

SEQUENCE LISTING

<160> NUMBER OF SEQ ID NOS: 18

<210> SEQ ID NO 1
<211> LENGTH: 1116
<212> TYPE: DNA
<213> ORGANISM: Homo sapiens

<400> SEQUENCE: 1

| | | | | | |
|---|---|---|---|---|---|
| ttgctgcttg | gggacctcct | tctagcctta | aatttcagct | catcaccttc | acctgccttg | 60 |
| gtcatggctc | tgctattctc | cttgatcctt | gccatttgca | ccagacctgg | attcctagcg | 120 |
| tctccatctg | gagtgcggct | ggtgggggc | ctccaccgct | gtgaagggcg | ggtggaggtg | 180 |
| gaacagaaag | gccagtgggg | caccgtgtgt | gatgacggct | gggacattaa | ggacgtggct | 240 |
| gtgttgtgcc | gggagctggg | ctgtggagct | gccagcggaa | ccctagtgg | tattttgtat | 300 |
| gagccaccag | cagaaaaaga | gcaaaaggtc | ctcatccaat | cagtcagttg | cacaggaaca | 360 |
| gaagatacat | tggctcagtg | tgagcaagaa | gaagtttatg | attgttcaca | tgatgaagat | 420 |
| gctggggcat | cgtgtgagaa | cccagagagc | tctttctccc | cagtcccaga | gggtgtcagg | 480 |
| ctggctgacg | gccctgggca | ttgcaaggga | cgcgtggaag | tgaagcacca | gaaccagtgg | 540 |
| tataccgtgt | gccagacagg | ctggagcctc | cgggccgcaa | aggtggtgtg | ccggcagctg | 600 |
| ggatgtggga | gggctgtact | gactcaaaaa | cgctgcaaca | agcatgccta | tggccgaaaa | 660 |
| cccatctggc | tgagccagat | gtcatgctca | ggacgagaag | caacccttca | ggattgccct | 720 |
| tctgggcctt | ggggaagaa | cacctgcaac | catgatgaag | acacgtgggt | cgaatgtgaa | 780 |
| gatccctttg | acttgagact | agtaggagga | gacaacctct | gctctgggcg | actggaggtg | 840 |
| ctgcacaagg | gcgtatgggg | ctctgtctgt | gatgacaact | ggggagaaaa | ggaggaccag | 900 |
| gtggtatgca | agcaactggg | ctgtgggaag | tccctctctc | cctccttcag | agaccggaaa | 960 |
| tgctatggcc | ctggggttgg | ccgcatctgg | ctggataatg | ttcgttgctc | aggggaggag | 1020 |
| cagtccctgg | agcagtgcca | gcacagattt | tgggggtttc | acgactgcac | ccaccaggaa | 1080 |
| gatgtggctg | tcatctgctc | aggatagtat | cctggt | | | 1116 |

<210> SEQ ID NO 2
<211> LENGTH: 347
<212> TYPE: PRT
<213> ORGANISM: Homo sapiens

<400> SEQUENCE: 2

Met Ala Leu Leu Phe Ser Leu Ile Leu Ala Ile Cys Thr Arg Pro Gly
1               5                   10                  15

Phe Leu Ala Ser Pro Ser Gly Val Arg Leu Val Gly Gly Leu His Arg
            20                  25                  30

Cys Glu Gly Arg Val Glu Val Glu Gln Lys Gly Gln Trp Gly Thr Val
        35                  40                  45

Cys Asp Asp Gly Trp Asp Ile Lys Asp Val Ala Val Leu Cys Arg Glu
    50                  55                  60

Leu Gly Cys Gly Ala Ala Ser Gly Thr Pro Ser Gly Ile Leu Tyr Glu
65                  70                  75                  80

Pro Pro Ala Glu Lys Glu Gln Lys Val Leu Ile Gln Ser Val Ser Cys
                85                  90                  95

Thr Gly Thr Glu Asp Thr Leu Ala Gln Cys Glu Gln Glu Glu Val Tyr
            100                 105                 110

Asp Cys Ser His Asp Glu Asp Ala Gly Ala Ser Cys Glu Asn Pro Glu
        115                 120                 125

-continued

```
Ser Ser Phe Ser Pro Val Pro Glu Gly Val Arg Leu Ala Asp Gly Pro
130                 135                 140

Gly His Cys Lys Gly Arg Val Glu Val Lys His Gln Asn Gln Trp Tyr
145                 150                 155                 160

Thr Val Cys Gln Thr Gly Trp Ser Leu Arg Ala Ala Lys Val Val Cys
                165                 170                 175

Arg Gln Leu Gly Cys Gly Arg Ala Val Leu Thr Gln Lys Arg Cys Asn
            180                 185                 190

Lys His Ala Tyr Gly Arg Lys Pro Ile Trp Leu Ser Gln Met Ser Cys
        195                 200                 205

Ser Gly Arg Glu Ala Thr Leu Gln Asp Cys Pro Ser Gly Pro Trp Gly
210                 215                 220

Lys Asn Thr Cys Asn His Asp Glu Asp Thr Trp Val Glu Cys Glu Asp
225                 230                 235                 240

Pro Phe Asp Leu Arg Leu Val Gly Gly Asp Asn Leu Cys Ser Gly Arg
                245                 250                 255

Leu Glu Val Leu His Lys Gly Val Trp Gly Ser Val Cys Asp Asp Asn
            260                 265                 270

Trp Gly Glu Lys Glu Asp Gln Val Val Cys Lys Gln Leu Gly Cys Gly
        275                 280                 285

Lys Ser Leu Ser Pro Ser Phe Arg Asp Arg Lys Cys Tyr Gly Pro Gly
290                 295                 300

Val Gly Arg Ile Trp Leu Asp Asn Val Arg Cys Ser Gly Glu Glu Gln
305                 310                 315                 320

Ser Leu Glu Gln Cys Gln His Arg Phe Trp Gly Phe His Asp Cys Thr
                325                 330                 335

His Gln Glu Asp Val Ala Val Ile Cys Ser Gly
            340                 345

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
cctggacgaa tcctgtgaag                                                      20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
ggtgggacca cagagagttg                                                      20

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
tcttctcatt cctgcttgtg g                                                    21
```

```
<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ggtctgggcc atagaactga                                                  20

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
gatggatgct accaaactgg a                                                21

<210> SEQ ID NO 8
<211> LENGTH: 24
<212> TYPE: DNA
<213> ORGANISM: Artificial
<220> FEATURE:
<223> OTHER INFORMATION: primer

<400> SEQUENCE: 8
ccaggtagct atggtactcc agaa                                             24

<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9
tgtaatgaaa gacggcacac c                                                21

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
tcttctttgg gtattgcttg g                                                21

<210> SEQ ID NO 11
<211> LENGTH: 22
<212> TYPE: DNA
<213> ORGANISM: Artificial
<220> FEATURE:
<223> OTHER INFORMATION: primer

<400> SEQUENCE: 11
actctcttcc agccatcttt ca                                               22

<210> SEQ ID NO 12
<211> LENGTH: 20
<212> TYPE: DNA
<213> ORGANISM: Artificial
<220> FEATURE:
<223> OTHER INFORMATION: primer
```

<400> SEQUENCE: 12
ataggtggtt tcgtggatgc                                                    20

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
tggagcaaca tgtggaactc                                                    20

<210> SEQ ID NO 14
<211> LENGTH: 18
<212> TYPE: DNA
<213> ORGANISM: Artificial
<220> FEATURE:
<223> OTHER INFORMATION: primer

<400> SEQUENCE: 14
cagcagccgg ttaccaag                                                      18

<210> SEQ ID NO 15
<211> LENGTH: 19
<212> TYPE: DNA
<213> ORGANISM: Artificial
<220> FEATURE:
<223> OTHER INFORMATION: primer

<400> SEQUENCE: 15
catgctgcaa agctgacaa                                                     19

<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16
ctttgcaatg gatgctctct t                                                  21

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
agaacatcat ccctgcatcc                                                    20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
cacattgggg gtaggaacac                                                    20

US 9,993,524 B2

PROPHYLACTIC OR THERAPEUTIC AGENT FOR HEPATIC DISEASES

SEQUENCE LISTING SUBMISSION VIA EFS-WEB

A computer readable text file, entitled "SequenceListing.txt," created on or about Oct. 22, 2014 with a file size of about 8 kb contains the sequence listing for this application and is hereby incorporated by reference in its entirety.

TECHNICAL FIELD

The present invention relates to a prophylactic or therapeutic agent for hepatic diseases and the like.

BACKGROUND ART

Metabolic syndrome is a modern disease that has rapidly surfaced along with the changes in the living environment in recent years, and various disease groups difficult to control such as type 2 diabetes, arteriosclerotic disease and the like are developed like falling of dominoes. In the series of the disease, what becomes marked together with obesity from the early stage is fatty liver. It has been recently clarified that several dozen percent of patients with fatty liver advance to a disease called non-alcoholic steatohepatitis (NASH). In NASH, a wide range of hepatic parenchyma becomes fibrotic in an alcohol independent manner, and cirrhosis and hepatic cancer are often developed further. While insulin sensitizer, antioxidant, liver supporting agent, anti-hyperlipidemia agent, depressor and the like are used for the treatment of NASH, an established treatment method does not exist, and the development of an effective therapeutic drug has been desired.

The accurate onset mechanism of NASH is still unknown. While a two-hit theory that inflammation and insulin resistance are combined with fatty liver, NASH is developed has been proposed, there is no conclusive experimental proof. As an animal model of NASH, a mouse loaded with MCD (methionine-choline deficient diet) or carbon tetrachloride can be mentioned; however, fibrosis after liver necrosis due to liver failure is the main with decreased body weight, and does not accurately reflect liver fibrosis in human patients with metabolic syndrome, which is caused by obesity and fatty liver due to overnutrition. Once an animal model of NASH capable of reproducing human pathology can be generated, a therapeutic drug for NASH can be screened for or evaluated.

While metabolic syndrome is based on the acquisition of insulin resistance associated with obesity, it has been clarified in recent years that chronic inflammation of adipose tissue is important. Sustained inflammation of adipose tissue due to obesity spreads in the entire body to induce systemic insulin resistance.

The present inventors have clarified in recent years that a key to the pathology is AIM (Apoptosis Inhibitor of Macrophage) as stated below (non-patent documents 1-4). AIM is specifically produced by macrophage and present in blood. Due to obesity, the blood concentration of AIM increases, AIM is incorporated into adipocyte by endocytosis via CD36, induces degradation of accumulated neutral fats (lipolysis), and releases free fatty acid from the adipocyte (non-patent document 5). The released fatty acid induces and maintains chronic inflammation in adipose tissues via stimulation of a toll-like receptor (non-patent document 6). In fact, in AIM knockout (KO) mouse, obesity does not result in chronic inflammation in the entire body including the adipose tissues and the liver, and does not produce insulin resistance, which in turn markedly suppresses the development of diabetes and arteriosclerosis (non-patent documents 4, 6). However, the involvement of AIM in the onset and progression of hepatic diseases, particularly NASH, has not been known heretofore.

DOCUMENT LIST

Non-Patent Documents non-patent document 1: J Exp Med 189: 413-422, 1999
non-patent document 2: J Biol Chem 276: 22910-22914, 2001
non-patent document 3: Am J Pathol 162: 837-847, 2003
non-patent document 4: Cell Metab 1: 201-213, 2005
non-patent document 5: Cell Metab 11: 479-492, 2010
non-patent document 6: PNAS 108: 12072-12077, 2011

SUMMARY OF THE INVENTION

Problems to be Solved by the Invention

The present invention aims to provide a prophylactic or therapeutic drug for hepatic diseases. In addition, the present invention aims to provide a new method for the evaluation of or screening for a prophylactic or therapeutic drug for hepatic diseases, and the like. Furthermore, another object of the present invention provides a diagnostic method of hepatic diseases.

Means of Solving the Problems

The present inventor studied the pathology of AIM knockout mouse made obese by loading a high fat diet and obtained a highly interesting finding that a pathology similar to the pathology of human NASH of (1) obesity, (2) preceding fatty liver, (3) fibrosis of hepatic parenchyma, and (4) highly frequent carcinogenesis occurs in a state where both chronic inflammation of the whole body including the liver and insulin resistance are suppressed. Therefrom it is considered that supplementation of AIM becomes the prophylaxis or treatment of a series of hepatic disease such as fatty liver, NASH and liver cancer.

The present inventors have conducted further investigations based on these findings, and completed the present invention.

Accordingly, the present invention provides
[1] a prophylactic or therapeutic agent for a hepatic disease, comprising AIM or a partial peptide thereof, or a nucleic acid comprising a base sequence encoding the same;
[2] a prophylactic or therapeutic agent for a hepatic disease, comprising a drug that induces expression of AIM or a drug that stabilizes AIM;
[3] the agent of [1] or [2], wherein the hepatic disease is fatty liver, non-alcoholic steatohepatitis, cirrhosis or liver cancer;
[4] a method of screening for a prophylactic or therapeutic agent for a hepatic disease, comprising using an animal obtained by loading a non-human mammal deficient in AIM expression with a high fat diet;
[5] the method of [4], comprising the following steps:
(1) a step of administering, under high fat diet loading conditions, a test substance to a non-human mammal deficient in AIM expression, (2) a step of observing any one or more items of the following properties of the non-human mammal deficient in AIM expression, which is administered with the test substance:
(i) liver weight,
(ii) liver fat amount,
(iii) liver fiber,
(iv) liver cancer, and
(v) inflammation response in liver, and
(3) a step of selecting a test substance that improves the aforementioned properties by comparison to non-administration of the test substance;
[6] the method of [4] or [5], wherein the hepatic disease is fatty liver, non-alcoholic steatohepatitis, cirrhosis or liver cancer;
[7] a method of evaluating a prophylactic or therapeutic effect of a prophylactic or therapeutic agent for a hepatic disease, comprising using an animal obtained by loading a non-human mammal deficient in AIM expression with a high fat diet;
[8] the method of [7], comprising the following steps:
(1) a step of administering, under high fat diet loading conditions, a prophylactic or therapeutic agent for a hepatic disease to a non-human mammal deficient in AIM expression,
(2) a step of observing any one or more items of the following properties of the non-human mammal deficient in AIM expression, which is administered with the prophylactic or therapeutic agent for a hepatic disease:
(i) liver weight,
(ii) liver fat amount,
(iii) liver fiber,
(iv) liver cancer,
(v) inflammation response in liver,
(3) a step of evaluating an effect of the prophylactic or therapeutic agent for a hepatic disease by comparison of the aforementioned properties to those of non-administration of the prophylactic or therapeutic agent for a hepatic disease;
[9] the method of [7] or [8], wherein the hepatic disease is fatty liver, non-alcoholic steatohepatitis, cirrhosis or liver cancer;
[10] a method of diagnosing a hepatic disease, comprising the following steps:
(1) a step of measuring the AIM concentration of a sample of a test subject,
(2) a step of comparing the aforementioned AIM concentration of the sample of the test subject with the AIM concentration of a sample of a healthy human,
(3) a step of judging that the test subject has a hepatic disease or has a high possibility of developing a hepatic disease, when the aforementioned AIM concentration of the sample of the test subject is lower than the AIM concentration of the sample of the healthy human;
[11] the method of [10], wherein the hepatic disease is fatty liver, non-alcoholic steatohepatitis, cirrhosis or liver cancer;
[12] a method for the prophylaxis or treatment of a hepatic disease, comprising administering an effective amount of AIM or a partial peptide thereof, or a nucleic acid comprising a base sequence encoding the same to a subject;
[13] a method for the prophylaxis or treatment of a hepatic disease, comprising administering an effective amount a drug that induces AIM expression or a drug that stabilizes AIM to a subject;

[14] the method of [12] or [13], wherein the hepatic disease is fatty liver, non-alcoholic steatohepatitis, cirrhosis or liver cancer;
[15] AIM or a partial peptide thereof, or a nucleic acid comprising a base sequence encoding the same, for use in the prophylaxis or treatment of a hepatic disease;
[16] AIM or a partial peptide thereof, or a nucleic acid comprising a base sequence encoding the same of [15], wherein the hepatic disease is fatty liver, non-alcoholic steatohepatitis, cirrhosis or liver cancer;
[17] a drug that induces AIM expression or a drug that stabilizes AIM, for use in the prophylaxis or treatment of a hepatic disease; and
[18] the drug of [17], wherein the hepatic disease is fatty liver, non-alcoholic steatohepatitis, cirrhosis or liver cancer.

Effect of the Invention

The present invention can provide a prophylactic or therapeutic agent for a hepatic disease, comprising AIM and the like as an active ingredient. In addition, according to the screening method using a hepatic disease model mouse of the present invention, a substance effective to the prophylaxis or treatment for hepatic diseases can be searched. In addition, using the hepatic disease model mouse of the present invention, effects of a known prophylactic or therapeutic agent for a hepatic disease can be evaluated. Furthermore, the present invention can provide a method for diagnosis of a hepatic disease by measuring AIM concentration in a sample of a test subject.

DESCRIPTION OF EMBODIMENTS

Figure 1:
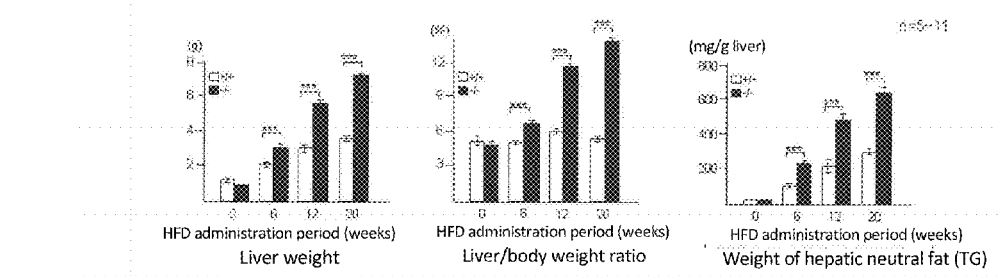
FIG. 1 shows graph indicating A: liver weight, ratio of liver weight to body weight, and weight of neutral fats in the liver of AIM KO mice and WT mice loaded with a high fat diet. mean±SEM, ***; $P<0.001$. B: hematoxylin-eosin (HE)-stained images of hepatic tissue sections of AIM KO mice and WT mice loaded with a high fat diet.
Figure 1:
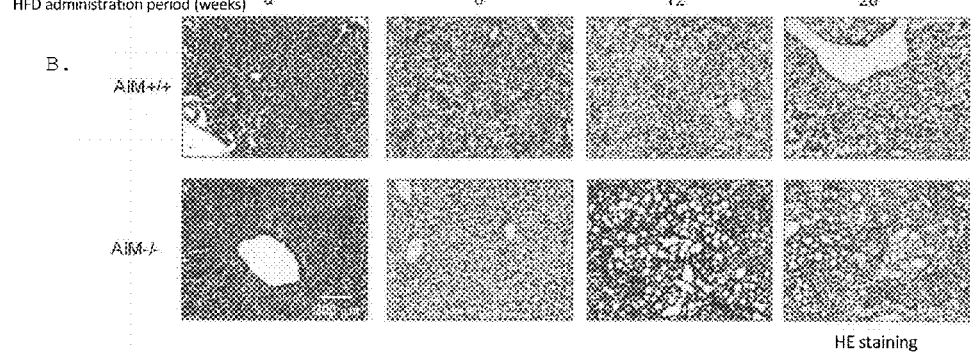

AIM in the present invention is a protein comprising the same or substantially the same amino acid sequence as the amino acid sequence shown in SEQ ID NO:2.

AIM may be, for example, a protein isolated and purified from macrophage, which is immunocyte of warm-blooded animals (e.g., human, mouse, rat, rabbit, sheep, swine, bovine, horse, cat, dog, monkey, chimpanzee, chicken and the like). It may also be a protein chemically synthesized or biochemically synthesized in a cell-free translation system. Alternatively, the protein may be a recombinant protein produced from a transformant incorporating a nucleic acid comprising a base sequence that encodes the above-described amino acid sequence.

Substantially the same amino acid sequence as the amino acid sequence shown in SEQ ID NO:2 refers to an amino acid sequence having a homology of about 60% or more, preferably about 70% or more, further preferably about 80% or more, particularly preferably about 90% or more, most preferably about 95% or more, to the amino acid sequence shown in SEQ ID NO:2, and the like. Here, "a homology" means a ratio (%) of identical amino acid residues and similar amino acid residues to all overlapping amino acid residues in the optimal alignment (preferably, the algorithm considers introduction of gaps on one or both sides of the sequence for the best alignment) where two amino acid sequences are aligned using a mathematical algorithm known in the technical field. "Similar amino acid" means an amino acid having similar physiochemical properties; examples thereof include amino acids classified under the same group, such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having a hydroxyl group (Ser, Thr) and amino acids having a small side-chain (Gly, Ala, Ser, Thr, Met). Substitution by such similar amino acids is expected not to change the phenotype of proteins (i.e., conservative amino acid substitution). Specific examples of the conservative amino acid substitution are known in the technical field and are described in various documents (see, for example, Bowie et al., Science, 247:1306-1310 (1990)).

Amino acid sequence homology in the present description can be calculated using the homology calculation algorithm NCBI BLAST (National Center for Biotechnology Information Basic Local Alignment Search Tool) under the following conditions (expectancy=10; gaps allowed; matrix=BLOSUM62; filtering=OFF). As examples of other algorithms for determination of amino acid sequence homology, the algorithm described in Karlin et al., Proc. Natl. Acad. Sci. USA, 90:5873-5877 (1993) [the algorithm is incorporated in the NBLAST and XBLAST programs (version 2.0) (Altschul et al., Nucleic Acids Res., 25:3389-3402 (1997))], the algorithm described in Needleman et al., J. Mol. Biol., 48:444-453 (1970) [the algorithm is incorporated in the GAP program in the GCG software package], the algorithm described in Myers and Miller, CABIOS, 4:11-17 (1988) [the algorithm is incorporated in the ALIGN program (version 2.0), which is part of the CGC sequence alignment software package], the algorithm described in Pearson et al., Proc. Natl. Acad. Sci. USA, 85:2444-2448 (1988) [the algorithm is incorporated in the FASTA program in the GCG software package] and the like can be mentioned, which can likewise be used preferably.

More preferably, substantially the same amino acid sequence as the amino acid sequence shown in SEQ ID NO:2 is an amino acid sequence having an identity of about 60% or more, preferably about 70% or more, further preferably about 80% or more, particularly preferably about 90% or more, and most preferably about 95% or more, to the amino acid sequence shown in SEQ ID NO:2.

As a protein comprising substantially the same amino acid sequence as the amino acid sequence shown in SEQ ID NO:2, for example, a protein comprising substantially the same amino acid sequence as the aforementioned amino acid sequence shown in SEQ ID NO:2, and having an activity substantially of the same quality as that of a protein comprising the amino acid sequence shown in SEQ ID NO:2 and the like are preferable. Here, the "activity" refers to, for example, an activity to suppress apoptosis of macrophage in atherosclerotic plaque, an activity to maintain or promote arteriosclerosis, an adipocyte differentiation suppressive activity, activity to melt lipid droplet of adipocyte, adipocyte reducing activity, CD36 binding activity, endocytosis activity to adipocyte, FAS binding activity, FAS function suppressive activity, antiobesity activity or the like. Being "substantially of the same quality" means that the activity thereof is qualitatively (e.g., physiologically or pharmacologically) the same. Therefore, it is preferable that the aforementioned activities be equivalent to each other, but the quantitative factors of these activities, such as the extent of activity (e.g., about 0.1 to about 10 times, preferably about 0.5 to about 2 times) and the molecular weight of the protein, may be different.

The aforementioned activities can be measured by a method known per se.

Examples of the AIM in the present invention also include what are proteins comprising (1) an amino acid sequence having 1 or 2 or more (preferably about 1 to 100, preferably about 1 to 50, further preferably about 1 to 10, particularly preferably 1 to several (2, 3, 4 or 5)) amino acids deleted from the amino acid sequence shown in SEQ ID NO:2, (2) an amino acid sequence having 1 or 2 or more (preferably about 1 to 100, preferably about 1 to 50, further preferably about 1 to 10, particularly preferably 1 to several (2, 3, 4 or 5)) amino acids added to the amino acid sequence shown in SEQ ID NO:2, (3) an amino acid sequence having 1 or 2 or more (preferably about 1 to 50, preferably about 1 to 10, further preferably 1 to several (2, 3, 4 or 5)) amino acids inserted in the amino acid sequence shown in SEQ ID NO:2, (4) an amino acid sequence having 1 or 2 or more (preferably about 1 to 50, preferably about 1 to 10, further preferably 1 to several (2, 3, 4 or 5)) amino acids substituted by other amino acids in the amino acid sequence shown in SEQ ID NO:2, or (5) an amino acid sequence comprising a combination thereof.

When an amino acid sequence has been inserted, deleted or substituted as described above, the position of the insertion, deletion or substitution is not particularly limited, as far as the activity of the protein is maintained.

AIM of the present invention is preferably a human AIM protein having the amino acid sequence shown in SEQ ID NO:2 (GenBank Accession No.: AAD01446), or a homologue thereof in other mammals [for example, mouse homologue registered in the GenBank as Accession No.: AAD01445 and the like].

In the present specification, the protein and peptide are described according to the common practice of peptide designation, wherein the left end indicates the N-terminal (amino terminal) and the right end indicates the C-terminal (carboxyl terminal). In AIM of the present invention including a protein comprising the amino acid sequence shown in SEQ ID NO:2, the C-terminal may be any of a carboxyl group (—COOH), carboxylate (—COO⁻), amide (—CONH$_2$) and ester (—COOR).

Here, as R in the ester, a $C_{1-6}$ alkyl group, for example, methyl, ethyl, n-propyl, isopropyl and n-butyl, a $C_{3-8}$ cycloalkyl group, for example, cyclopentyl and cyclohexyl, a $C_{6-12}$ aryl group, for example, phenyl and α-naphthyl, a phenyl-$C_{1-2}$ alkyl group, for example, benzyl and phenethyl, a $C_{7-14}$ aralkyl group, for example, an α-naphthyl-$C_{1-2}$ alkyl group, for example, α-naphthylmethyl, a pivaloyloxymethyl group; and the like can be used.

When the AIM of the present invention has a carboxyl group (or carboxylate) at a position other than the C-terminal, a protein wherein the carboxyl group is amidated or esterified is also included in the protein of the present invention. In this case, as the ester, the above-described ester at the C terminal, and the like, for example, are used.

Furthermore, the AIM of in the present invention also includes a protein wherein the amino group of the N-terminal amino acid residue is protected by a protecting group (e.g., $C_{1-6}$ acyl groups such as $C_{1-6}$ alkanoyls such as formyl group and acetyl group, and the like); a protein wherein the glutamine residue that may be produced upon cleavage at the N terminal in vivo has been converted to pyroglutamic acid, a protein wherein a substituent (e.g., —OH, —SH, amino group, imidazole group, indol group, guanidino group and the like) on a side chain of an amino acid in the molecule is protected by an appropriate protecting group (e.g., $C_{1-6}$ acyl groups such as $C_{1-6}$ alkanoyl groups such as formyl group and acetyl group, and the like), a conjugated peptide such as what is called a glycopeptide having a sugar chain bound thereto, and the like.

The partial peptide of AIM (hereinafter sometimes to be abbreviated simply as "the partial peptide of the present invention") may be any as long as it is a peptide having the above-mentioned partial amino acid sequence of AIM, and having an activity substantially of the same quality as AIM. Here, the "activity substantially of the same quality" is as defined above. In addition, the "activity substantially of the same quality" can be measured in the same manner as in the case of AIM.

Since AIM comprises 3 SRCR (Scavenger-Receptor Cysteine-Rich) domains comprising a large amount of cysteine, the respective SRCR domains can be used as the partial peptide of the present invention. To be specific, for example, of the amino acid sequence shown in SEQ ID NO:2, partial amino acid sequences respectively comprising SRCR1 domain (amino acid Nos. 24-125 of the amino acid sequence shown in SEQ ID NO:2), SRCR2 domain (amino acid Nos. 138-239 of the amino acid sequence shown in SEQ ID NO:2), and SRCR3 domain (amino acid Nos. 244-346 of the amino acid sequence shown in SEQ ID NO:2), partial amino acid sequence comprising any combination of SRCR domains and the like can be used. The size of the partial peptide of the present invention is not particularly limited as long as it comprises the above-mentioned functional domain. The partial peptide preferably comprises not less than 50 partial amino acid sequences, more preferably not less than 100 partial amino acid sequences, further preferably not less than 200 partial amino acid sequences. The partial amino acid sequences may be a single continued partial amino acid sequence, or discontinuous plural partial amino acid sequences linked to each other.

In addition, the C-terminal of the partial peptide of the present invention may be any of a carboxyl group (—COOH), carboxylate (—COO⁻), amide (—CONH$_2$) and ester (—COOR). Here, examples of the R in ester include, those similar to the examples recited above for AIM. When the partial peptide of the present invention has a carboxyl group (or carboxylate) at a position other than the C-terminal, the carboxyl group may be amidated or esterified, which is also encompassed in the partial peptide of the present invention. As the ester in this case, for example, those similar to the ester at the C-terminal and the like are used.

Furthermore, in the partial peptide of the present invention, in the same manner as in the above-mentioned AIM, the amino group of the N terminal amino acid residue may be protected with a protecting group, the glutamine residue at the N terminal may be converted to pyroglutamic acid, a substituent on the side chain of the amino acid in a molecule may be protected with a suitable protecting group, or the partial peptide may be a composite peptide wherein a sugar chain is bonded (so-called glycopeptide and the like), and the like.

AIM or a partial peptide thereof to be used in the present invention may be in the form of a salt. For example, salts with physiologically acceptable acid (e.g., inorganic acid, organic acid), base (e.g., alkali metal salt) and the like are used, and physiologically acceptable acid addition salts are preferable. Useful salts include, for example, salts with inorganic acids (e.g., hydrochloric acid, phosphoric acid, hydrobromic acid, sulfuric acid) or salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

AIM can be produced from a macrophage of the aforementioned mammals by a protein purification method known per se. To be specific, AIM or a salt thereof can be prepared by homogenizing mammalian macrophage, removing cell debris by low-speed centrifugation, centrifuging the supernatant at a high speed to precipitate a cell membrane-comprising fraction, and subjecting the supernatant to chromatography such as reversed-phase chromatography, ion exchange chromatography, affinity chromatography and the like, and the like.

AIM or a partial peptide thereof can also be produced according to a publicly known method of peptide synthesis (hereinafter full-length AIM and a partial peptide thereof are comprehensively referred simply to as AIM in the explanation of the chemical synthesis thereof, unless otherwise specified).

The method of peptide synthesis may be any of, for example, a solid phase synthesis process and a liquid phase synthesis process. A desired protein can be produced by condensing a partial peptide or amino acid capable of constituting AIM with the remaining portion, and removing any protecting group the resultant product may have.

Here, the condensation and the protecting group removal are conducted in accordance with methods known per se, for example, the methods indicated in (1) and (2) below:
(1) M. Bodanszky and M. A. Ondetti: *Peptide Synthesis*, Interscience Publishers, New York (1966)
(2) Schroeder and Luebke: *The Peptide*, Academic Press, New York (1965).

AIM thus obtained can be purified or isolated by a known method of purification. Here, as examples of the method of purification, solvent extraction, distillation, column chromatography, liquid chromatography, recrystallization, combinations thereof and the like can be mentioned.

When thus obtained AIM is in a free form, the free form can be converted into a suitable salt form by a known method or an analogue thereto, and on the other hand, when the AIM is obtained in the form of a salt, it can be converted into the free form or in the form of a different salt by a known method or an analogue thereto.

Furthermore, AIM can also be produced by culturing a transformant comprising a nucleic acid encoding the same, and separating and purifying AIM from the obtained culture. The nucleic acid encoding AIM or a partial peptide thereof may be DNA or RNA, or DNA/RNA chimera, preferably DNA. Additionally, the nucleic acid may be double-stranded or single-stranded. In the case of a double-stranded nucleic acid, it may be a double-stranded DNA, a double-stranded RNA, or a DNA:RNA hybrid. In the case of a single strand, it may be a sense strand (that is, coding strand), or an antisense strand (that is, non-coding strand).

Examples of the DNA encoding AIM or a partial peptide thereof include genome DNA, cDNA derived from macrophage of warm-blooded animal (e.g., human, bovine, monkey, horse, swine, sheep, goat, dog, cat, guinea pig, rat, mouse, rabbit, hamster, chicken and the like), synthetic DNA and the like. Genome DNA encoding AIM or a partial peptide thereof can be directly amplified by Polymerase Chain Reaction (hereinafter to be abbreviated as "PCR method") by using, as a template, a genome DNA fraction prepared from any cell of the aforementioned animals [for example, hepatocyte, splenocyte, nerve cell, glial cell, pancreatic β cell, myelocyte, mesangial cell, Langerhans' cell, epidermal cell, epithelial cell, goblet cell, endothelial cell, smooth muscle cell fibroblast, fibrocyte, myocyte, adipocyte, immunocyte (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte or interstitial cell, or corresponding progenitor cell, stem cell or cancer cell thereof, and the like] of a human or other warm-blooded animal (e.g., monkey, bovine, horse, swine, sheep, goat, rabbit, mouse, rat, guinea pig, hamster, chicken, and the like), or any tissue where such cells are present [for example, brain or any portion of the brain (e.g., olfactory bulb, amygdaloid nucleus, basal ganglia, hippocampus, thalamus, hypothalamus, subthalamic nucleus, cerebral cortex, medulla oblongata, cerebellum), spinal cord, hypophysis, stomach, pancreas, kidney, liver, gonad, thyroid, gallbladder, bone marrow, adrenal gland, skin, lung, gastrointestinal tract (e.g., large intestine, small intestine), blood vessel, heart, thymus, spleen, submandibular gland, peripheral blood, prostate, testicle, ovary, placenta, uterus, bone, joint, adipose tissue (e.g., brown adipose tissue, white adipose tissue), skeletal muscle and the like], and cDNA encoding AIM or a partial peptide thereof can also be directly amplified by PCR method and Reverse Transcriptase-PCR (hereinafter to be abbreviated as "RT-PCR method") by using, as a template, a total RNA or mRNA fraction prepared from macrophage, respectively. Alternatively, the genome DNA and cDNA encoding AIM or a partial peptide thereof can also be cloned by colony or plaque hybridization method or PCR method and the like from a genome DNA library and cDNA library prepared by inserting the above-mentioned genome DNA and total RNA or a fragment of mRNA into a suitable vector. The vector used for the library may be any of a bacteriophage, a plasmid, a cosmid, a phagemid and the like.

Examples of the DNA encoding AIM include a DNA comprising the same or substantially the same base sequence as the base sequence shown by base Nos. 64 to 1107 of the SEQ ID NO: 1 and the like.

As the DNA comprising the same or substantially the same base sequence as the base sequence shown by base Nos. 64 to 1107 of the SEQ ID NO: 1, a DNA comprising a base sequence having a homology of not less than about 60%, preferably not less than about 70%, more preferably not less than about 80%, particularly preferably not less than about 90%, with the base sequence shown by base Nos. 64 to 1107 of the SEQ ID NO: 1, and encoding a protein having an activity substantially of the same quality as the aforementioned AIM and the like are used.

Base sequence homology in the present description can be calculated using the homology calculation algorithm NCBI BLAST (National Center for Biotechnology Information Basic Local Alignment Search Tool) under the following conditions (expectancy=10; gap allowed; filtering=ON; match score=1; mismatch score=−3). As preferable examples of other algorithms for determining base sequence homology, the above-described amino acid sequence homology calculation algorithm can also be mentioned.

The DNA encoding AIM is preferably a DNA comprising a base sequence encoding human AIM protein shown by the base sequence shown by base Nos. 64 to 1107 of the SEQ ID NO: 1 (GenBank accession No: AF011429), or a homologue thereof in other mammal [for example, mouse homologue registered in GenBank as accession No: AF011428 and the like].

The DNA encoding the partial peptide of the present invention may be any as long as it comprises a base sequence encoding a peptide comprising an amino acid sequence the same or substantially the same as a part of the amino acid sequence shown in SEQ ID NO:2. Specifically, as a DNA encoding the partial peptide of the present invention, (1) a DNA comprising a partial base sequence shown by the base sequence shown by base Nos. 64 to 1107 of the SEQ ID NO: 1, or (2) a DNA comprising a base sequence having a homology of not less than about 60%, preferably not less than about 70%, more preferably not less than about 80%, particularly preferably not less than about 90%, with a DNA comprising a partial base sequence shown by base Nos. 64 to 1107 of the SEQ ID NO: 1, and encoding a protein having an activity substantially of the same quality as the aforementioned AIM and the like are used.

A DNA encoding AIM or a partial peptide thereof can be cloned by amplifying a synthesized DNA primer having a part of a base sequence encoding the AIM or a partial peptide thereof by PCR method, or hybridizing a DNA incorporated into a suitable expression vector with a labeled DNA fragment or synthetic DNA encoding a part or whole region of AIM. Hybridization can be conducted according to a method known per se or a method based thereon, for example, a method described in Molecular Cloning, 2nd edition (J. Sambrook et al., Cold Spring Harbor Lab. Press, 1989) and the like. When a commercially available library is used, hybridization can be conducted according to the method described in the instruction manual attached thereto. Hybridization can preferably be conducted under highly stringent conditions.

As examples of the highly stringent conditions, conditions of a hybridization reaction in 6×SSC (sodium chloride/sodium citrate) at 45° C. followed by washing in 0.2×SSC/0.1% SDS at 65° C. once or more and the like can be mentioned. Those skilled in the art are able to easily obtain desired stringency by changing the salt concentration of the hybridization solution, hybridization reaction temperature, probe concentration, probe length, the number of mismatches, hybridization reaction time, the salt concentration of the washing solution, washing temperature and the like as appropriate. When a commercially available library is used, hybridization can be conducted according to the method described in the instruction manual attached to the library.

An expression vector comprising DNA that encodes AIM or a partial peptide thereof can be produced by, for example, cutting out a desired DNA fragment from the DNA that encodes AIM, and joining the DNA fragment downstream of a promoter in an appropriate expression vector.

As the expression vector, plasmid derived from *Escherichia coli* (e.g., pBR322, pBR325, pUC12, pUC13); animal cell expression plasmid (e.g., pA1-11, pXT1, pRc/CMV, pRc/RSV, pcDNAI/Neo); animal virus vectors such as retrovirus, vaccinia virus, adenovirus and the like, and the like are used.

The promoter may be any promoter, as long as it is appropriate for the host used to express the gene.

For example, when the host is an animal cell, SRα promoter, SV40 promoter, LTR promoter, CMV (cytomegalovirus) promoter, RSV (Rous sarcoma virus) promoter, MoMuLV (Moloney murine leukemia virus) LTR, HSV-TK (simple herpes virus thymidine kinase) promoter and the like are used. Of these, CMV promoter, SRα promoter and the like are preferable.

When the host is a bacterium of the genus *Escherichia*, the trp promoter, the lac promoter, the recA promoter, the λP$_L$ promoter, the lpp promoter, the T7 promoter and the like are preferred.

Useful expression vectors include, in addition to the above, those optionally harboring an enhancer, a splicing signal, a polyA addition signal, a selection marker, an SV40 replication origin (hereinafter also abbreviated as SV40ori) and the like. As examples of the selection marker, the dihydrofolate reductase (hereinafter also abbreviated as dhfr) gene [methotrexate (MTX) resistance], the ampicillin resistance gene (hereinafter also abbreviated as Amp$^r$), the neomycin resistance gene (hereinafter also abbreviated as Neo$^r$, G418 resistance) and the like can be mentioned. In particular, when a Chinese hamster cell lacking the dhfr gene is used in combination with the dhfr gene as the selection marker, a target gene can also be selected using a thymidine-free medium.

Where necessary, a base sequence encoding a signal sequence suitable for a host (signal codon) may be added (or substituted with native signal codon) to the 5'-terminal side of a DNA encoding AIM or a partial peptide thereof. For example, when the host is the genus *Escherichia*, PhoA signal sequence, OmpA signal sequence and the like are used; when the host is an animal cell, insulin signal sequence, α-interferon signal sequence, antibody molecule signal sequence and the like are used.

AIM or a partial peptide thereof can be produced by transforming a host with an expression vector comprising the above-mentioned DNA encoding AIM or a partial peptide thereof, and cultivating the obtained transformant.

As the host, for example, the genus *Escherichia*, animal cell and the like are used.

As the genus *Escherichia*, for example, *Escherichia coli* K12·DH1 [Proc. Natl. Acad. Sci. USA), vol. 60, 160(1968)], *Escherichia coli* JM103 [Nucleic Acids Research, vol. 9, 309(1981)], *Escherichia coli* JA221 [Journal of Molecular Biology, vol. 120, 517(1978)], *Escherichia coli* HB101 [Journal of Molecular Biology, vol. 41, 459(1969)], *Escherichia coli* C600 [Genetics, vol. 39, 440(1954)] and the like are used.

As the animal cell, for example, monkey COS-7 cell, monkey Vero cell, Chinese hamster ovary cell (hereinafter to be abbreviated as CHO cell), dhfr gene-deficient CHO cell (hereinafter to be abbreviated as CHO(dhfr⁻) cell), mouse L cell, mouse AtT-20 cell, mouse myeloma cell, ratGH3 cell, human FL cell and the like are used.

Transformation can be carried out according to the kind of host in accordance with a publicly known method.

The genus *Escherichia* can be transformed, for example, in accordance with the methods described in Proc. Natl. Acad. Sci. USA, vol. 69, 2110 (1972), Gene, vol. 17, 107 (1982) and the like.

An animal cell can be transformed, for example, in accordance with a method described in Saibo Kogaku (Cell Engineering), extra issue 8, Shin Saibo Kogaku Jikken Protocol (New Cell Engineering Experimental Protocol), 263-267 (1995), published by Shujunsha, or Virology, Vol. 52, 456 (1973).

Cultivation of a transformant can be carried out according to the kind of host in accordance with a publicly known method.

As an example of the medium used to cultivate a transformant whose host is a bacterium of the genus *Escherichia*, a M9 medium supplemented with glucose and a casamino acid [Miller, Journal of Experiments in Molecular Genetics, 431-433, Cold Spring Harbor Laboratory, New York 1972] is preferable. As required, in order to increase promoter efficiency, a chemical agent such as 3β-indolylacrylic acid may be added to the medium.

Cultivation of a transformant whose host is a bacterium of the genus *Escherichia* is normally carried out at about 15° C. to about 43° C. for about 3 to about 24 hours. As necessary, the culture may be aerated or agitated.

Useful medium for cultivating a transformant whose host is an animal cell include, for example, minimum essential medium (MEM) comprising about 5-about 20% fetal bovine serum [Science, vol. 122, 501 (1952)], Dulbecco's modified Eagle medium (DMEM) [Virology, vol. 8, 396(1959)], RPMI1640 medium [The Journal of the American Medical Association, vol. 199, 519(1967)], 199 medium [Proceeding of the Society for the Biological Medicine, vol. 73, 1(1950)] and the like. The medium's pH is preferably about 6 to about 8. Cultivation is normally carried out at about 30° C. to about 40° C. for about 15 to about 60 hours. As necessary, the culture may be aerated or agitated.

As described above, AIM can be produced in a cell of the transformant or outside the cell.

AIM or a partial peptide thereof can be separated and purified from the culture obtained by cultivating the aforementioned transformant according to a method known per se.

For example, when AIM or a partial peptide thereof is extracted from a cultured bacterium or cytoplasm of cell, a method is used as appropriate wherein bacteria or cells are collected by a known means, suspended in an appropriate buffer solution, and disrupted by means of sonication, lysozyme and/or freeze-thawing and the like, after which a crude extract of soluble protein is obtained by centrifugation or filtration. The buffer solution may comprise a protein denaturant such as urea or guanidine hydrochloride and a surfactant such as Triton X-100™. In addition, when AIM or a partial peptide thereof is secreted outside the fungus (cell), a method of separating a culture supernatant by centrifugation, filtration or the like from a culture, and the like are used.

Isolation and purification of AIM or a partial peptide thereof contained in the thus-obtained soluble fraction and culture supernatant can be conducted according to a method know per se. Useful methods include methods based on solubility, such as salting-out and solvent precipitation; methods based mainly on molecular weight differences, such as dialysis, ultrafiltration, gel filtration, and SDS-polyacrylamide gel electrophoresis; methods based on charge differences, such as ion exchange chromatography; methods based on specific affinity, such as affinity chromatography; methods based on hydrophobicity differences, such as reversed-phase high performance liquid chromatography; and methods based on isoelectric point differences, such as isoelectric focusing. These methods can be combined as appropriate.

The presence of the thus-obtained AIM or a partial peptide thereof can be confirmed by enzyme immunoassay, Western blotting and the like using an antibody against AIM.

AIM or a partial peptide thereof or a salt thereof or nucleic acid comprising a base sequence encoding AIM or a partial peptide thereof (sometimes to be indicated as AIMs here) obtained as mentioned above can be provided as an agent for the prophylaxis of the onset or the treatment of hepatic diseases.

In the present invention, a drug that induces AIM expression and a drug that stabilizes AIM can also be used instead of the AIMs.

Examples of the drug that induces AIM expression include a compound having an AIM transcription activity and the like, and examples of the compound include a transcription factor capable of binding to promoter region ofthe AIM gene and the like. The present inventor has also found that AIM is expressed in macrophage. Therefore, as a drug that induces AIM expression, a macrophage differentiation inducer can be mentioned. The macrophage differentiation inducer is not particularly limited as long as it can induce differentiation of macrophage from progenitor cells such as granulocyte-macrophage colony forming cell (CFU-GM), macrophage colony forming cell (CFU-M) and the like, and granulocyte-macrophage colony stimulating factor (GM-CSF), macrophage colony stimulating factor (M-CSF) and the like can be used. The transcription factor, GM-CSF, M-CSF may be proteins isolated and purified from mammalian tissues and cells by the aforementioned known means, or may be proteins chemical synthesized or biochemically synthesized in a cell-free translation system. Alternatively, they may be recombinant proteins produced from transformants introduced with a nucleic acid comprising a base sequence encoding the above-mentioned proteins.

Examples of the drug that stabilizes AIM include a compound inhibiting degradation of AIM, a compound inhibiting excretion into urine and the like. Examples of the compound inhibiting degradation include protease inhibitor, proteasome inhibitor and the like. Examples of the protease inhibitor include serine protease inhibitor (4-(2-aminoethyl) benzenesulfonyl fluoride hydrochloride (AEBSGF), aprotinin, trypsin inhibitor and the like), cysteine protease inhibitor (E-64, leupeptin and the like) and the like. Examples of the proteasome inhibitor include lactacystin, MG-115, MG-132, proteasome inhibitor I and the like. Examples of the compound inhibiting excretion into urine include a compound that confers AIM with a molecular weight preventing passage through glomerular basement membrane. As shown in the below-mentioned Examples, since binding of IgM to AIM could be confirmed, IgM can be mentioned as a compound inhibiting excretion of AIM into urine. However, since administration of IgM per se is feared to cause side effects in the immune system, a fusion protein obtained by fusion of Fc fragment of IgM which is a binding site to AIM and a protein having a molecular weight of the level preventing filtration by renal tubule and excretion into urine is preferably used. While the protein to be fused is not limited, a protein with less fear of side effect is preferable and, for example, albumin can be used. The binding may be a direct one or via a hinge region. Examples of the hinge region include tandem FLAG tags. Such molecule can be produced by linking a gene encoding each and as a single recombinant protein by a conventional method.

In the below-mentioned Examples of the present invention, AIM knockout mouse showed promoted onset of hepatic diseases under a high fat diet loading conditions as compared to wild-type (WT) mouse. Particularly, the hepatic diseases are similar to the pathology of non-alcoholic steatohepatitis (NASH), and progression to cirrhosis and hepatocyte cancer, which are the characteristics of the disease, were confirmed to be reproducible. From the above, AIMs, a drug that induces the expression of AIM or a drug that stabilizes AIM, or a compound capable of substituting the function of AIM, which can be searched for by the below-mentioned screening method, is suggested to prevent the onset and progression of hepatic diseases and treat hepatic diseases.

The hepatic diseases to be the application target of the pharmaceutical composition of the present invention comprising AIMs, a drug that induces expression of AIM or a drug that stabilizes AIM are, for example, fatty liver, NASH, cirrhosis, and liver cancer. In another aspect, the hepatic diseases to be the application target of the pharmaceutical composition of the present invention comprising AIMs, a drug that induces expression of AIM or a drug that stabilizes AIM are, for example, hepatic diseases associated with activation of hepatic stellate cells. An index of the activation of hepatic stellate cell is, for example, expression of αSMA (α-smooth muscle actin) mRNA. Therefore, the hepatic disease may be a hepatic disease wherein αSMA mRNA is significantly highly expressed as compared to normal hepatic tissues. In still another aspect, the hepatic disease may be a hepatic disease wherein TGFβ1 or Collagen 4A1 is significantly highly expressed as compared to normal hepatic tissues.

The pharmaceutical composition of the present invention comprising AIMs, a drug that induces expression of AIM or a drug that stabilizes AIM is of low toxicity, and can be administered as a liquid as it is, or as an appropriate dosage form of pharmaceutical composition, to humans or other warm-blooded mammals (e.g., mice, rats, rabbits, sheep, pigs, bovines, cats, dogs, monkeys and the like) orally or parenterally (e.g., intravascular administration, subcutaneous administration and the like).

As examples of the composition for parenteral administration, injections, suppositories and the like are used; the injections may include dosage forms such as intravenous injections, subcutaneous injections, intracutaneous injections, intramuscular injections and drip infusion injections. Such an injection can be prepared according to a publicly known method. An injection can be prepared by, for example, dissolving, suspending or emulsifying the above-described AIMs, a drug that induces expression of AIM or a drug that stabilizes AIM of the present invention in a sterile aqueous or oily solution in common use for injections. As examples of aqueous solutions for injection, physiological saline, an isotonic solution comprising glucose or another auxiliary drug, and the like can be used, which may be used in combination with an appropriate solubilizer, for example, alcohol (e.g., ethanol), polyalcohol (e.g., propylene glycol, polyethylene glycol), non-ionic surfactant [e.g., polysorbate 80, HCO-50 (polyoxyethylene (50 mol) adduct of hydrogenated castor oil)] and the like. As examples of oily solutions, sesame oil, soybean oil and the like can be used, which may be used in combination with benzyl benzoate, benzyl alcohol and the like as solubilizers. The prepared injection solution is preferably filled in an appropriate ampoule. Suppositories used for rectal administration may be prepared by mixing the above-described AIMs, a drug that induces expression of AIM or a drug that stabilizes AIM of the present invention with an ordinary suppository base.

As the composition for oral administration, solid or liquid dosage forms, specifically tablets (including sugar-coated tables and film-coated tablets), pills, granules, powders, capsules (including soft capsules), syrups, emulsions, suspensions and the like can be mentioned. Such a composition is produced by a publicly known method, and may comprise a carrier, diluent or excipient in common use in the field of pharmaceutical making. As examples of the carrier or excipient for tablets, lactose, starch, sucrose, magnesium stearate and the like can be used.

The above-mentioned pharmaceutical composition for parenteral or oral administration is conveniently prepared in a medication unit dosage form suitable for the dosage of the active ingredient. As examples of such a medication unit dosage form, tablets, pills, capsules, injections (ampoules), and suppositories can be mentioned. It is preferable that the above-mentioned AIMs, a drug that induces expression of AIM or a drug that stabilizes AIM of the present invention be contained at, for example, normally 5 to 500 mg, particularly 5 to 100 mg for injections, or 10 to 250 mg for other dosage forms, per medication unit dosage form.

While the dose of the above-mentioned prophylactic or therapeutic agent of the present invention comprising AIMs, a drug that induces expression of AIM or a drug that stabilizes AIM varies depending on the subject of administration, target disease, symptoms, route of administration and the like; for example, when the agent is used for the treatment/prevention of hepatic diseases in adult, it is convenient to administer the AIMs of the present invention usually at about 0.01 to 20 mg/kg body weight, preferably about 0.1 to 10 mg/kg body weight, and more preferably about 0.1 to 5 mg/kg body weight, based on a single dose, about 1 to 5 times a day, preferably about 1 to 3 times a day, by intravenous injection. In the case of other modes of parenteral administration and oral administration, similar doses may be administered. In case the symptom is particularly severe, the dose may be increased according to the symptom.

Each of the aforementioned compositions may comprise any other active ingredients that do not produce an unwanted interaction when formulated with the above-mentioned AIMs, a drug that induces expression of AIM or a drug that stabilizes AIM.

Furthermore, the AIMs, the drug that induces expression of AIM or the drug that stabilizes AIM of the present invention may be used in combination with other drugs useful for the treatment of hepatic diseases, such as insulin sensitizers (e.g., thiazolidine derivatives such as rosiglitazone, pioglitazone and the like, and the like, biguanides such as metformin, buformin and the like); antioxidants (e.g., vitamin E, vitamin C, betaine, EPL (Polyenephosphatidylcholine) etc.); liver supporting agents (e.g., ursodeoxycholic acid (UDCA) etc.); anti-hyperlipidemia agents (e.g., fibrate drugs, probucol, statin drugs etc.); depressors (e.g., angiotensin II receptor antagonists etc.); glycyrrhizin preparation; Chinese herbal medicines (e.g., shosaikoto etc.); anticancer agents and the like. The AIMs, the drug that induces expression of AIM or the drug that stabilizes AIM of the present invention and the above-described drugs may be administered to the patient at one time or different times.

As mentioned above, it was confirmed that AIM knockout mouse highly frequency develops hepatic diseases similar to the pathology of non-alcoholic steatohepatitis (NASH) under high fat diet loading conditions, as compared to wild-type mouse, and further progresses to cirrhosis and hepatocyte cancer. This suggests that AIM knockout mouse under high fat diet loading conditions can be provided as a new model mouse of hepatic diseases. Therefore, the present invention provides a screening method for an agent for the prophylaxis or treatment of hepatic diseases, which uses an animal obtained by loading a non-human mammal deficient in AIM expression with a high fat diet.

A non-human mammal deficient in AIM expression means a non-human mammal having the expression of endogenous AIM inactivated therein, including AIM KO animals prepared from an ES cell having the AIM knocked out (KO) therein, as well as knockdown (KD) animals having the expression of the AIM inactivated by antisense or RNAi technology therein, and the like. Here, "knocked out (KO)" means that the production of complete mRNA is prevented by destroying or removing the endogenous gene, whereas "knocked down (KD)" means that translation from mRNA into protein is inhibited to inactivate the expression of the endogenous gene. Hereinafter, the AIM KO/KD animal of the present invention is sometimes simply referred to as "the KO/KD animal of the present invention". The AIM KO animal of the present invention is disclosed in Miyazaki T. et al. (J. Exp. Med., 189, 413-422, 1999).

"A non-human mammal" that can be a subject of the present invention is not particularly limited, as long as it is a non-human mammal for which a transgenic system has been established; examples include mice, rats, bovines, monkeys, pigs, sheep, goat, rabbits, dogs, cats, guinea pigs, hamsters, rats, mice and the like. Rabbits, dogs, cats, guinea pigs, hamsters and the like are preferable; in particular, from the viewpoint of the preparation of disease model animals, rodents, which have relatively short periods of ontogeny and life cycles, and which are easy to propagate, are more preferable; particularly, mice (e.g., C57BL/6 strain, BALB/c strain, DBA2 strain and the like as pure strains, B6C3F$_1$ strain, BDF$_1$ strain, B6D2F$_1$ strain, ICR strain and the like as hybrid strains) and rats (e.g., Wistar, SD and the like) are preferable.

In addition to mammals, birds such as chickens can be used for the same purpose as that of "non-human mammals" being subjects of the present invention.

A specific means for knocking out the AIM is disclosed in the aforementioned Miyazaki T. et al. (J. Exp. Med., 189, 413-422, 1999). As other known general methods, there can be preferably used a method comprising isolating the AIM (genomic DNA) derived from the subject non-human mammal by a conventional method, and integrating a DNA strand having a DNA sequence constructed to consequently inactivate the gene by, for example, (1) destroying the function of the exon or promoter by inserting another DNA fragment (e.g., drug resistance gene, reporter gene and the like) into the exon portion or promoter region, or (2) cutting out the entire or a portion of the AIM using the Cre-loxP system or Flp-frt system to delete the gene, or (3) inserting a stop codon into the protein coding region to prevent the translation into complete protein, or (4) inserting a DNA sequence that stops the transcription of the gene (e.g., polyA addition signal and the like) into the transcription region to prevent the synthesis of complete mRNA, (hereinafter abbreviated as targeting vector), at the AIM gene locus of the subject non-human mammal by homologous recombination, and the like.

The homologous recombinant can be acquired by, for example, introducing the above-described targeting vector into an embryonic stem cell (ES cell).

An ES cell refers to a cell derived from an inner cell mass (ICM) of a fertilized egg in the blastocyst stage, and can be cultivated and maintained while keeping the undifferentiated state in vitro. ICM cells are destined to form the embryo body, being stem cells on which all tissues, including germ cells, are based. The ES cell used may be of an established cell line, or of a cell line newly established in accordance with the method of Evans and Kaufman (Nature, vol. 292, p. 154, 1981). For example, in the case of mouse ES cells, ES cells derived from a 129 mouse strain are currently generally used, but the immunological background thereof is unclear; for the purposes of acquiring ES cells of a pure strain instead thereof with an immunologically clear genetic background and the like, an ES cell established from a C57BL/6 mouse or from a BDF$_1$ mouse (F$_1$ of C57BL/6 and DBA/2), wherein the small number of ova collectable from C57BL/6 has been improved by crossing with DBA/2, and the like can also be used suitably. In addition to being advantageous in that the number of ova collectable is high, and that the ova are robust, BDF$_1$ mice have the C57BL/6 mouse as the background thereof; therefore, ES cells derived therefrom can be used advantageously in that, when preparing a disease model mouse, the genetic background can be replaced with that of the C57BL/6 mouse by back-crossing with a C57BL/6 mouse. ES cells can be differentiated into a wide variety of types of cell, including parietal muscle, visceral muscles, and cardiac muscle, by monolayer culture until the reach of a high density, or suspension culture until the formation of cell aggregates, under appropriate conditions [M. J. Evans and M. H. Kaufman, Nature vol. 292, p. 154, 1981; G. R. Martin, Proceedings of the National Academy of Sciences, USA (Proc. Natl. Acad. Sci. U.S.A.), vol. 78, p. 7634, 1981; T. C. Doetschman et al., Journal of Embryology and Experimental Morphology, vol. 87, p. 27, 1985]; the cell of a non-human mammal deficient in AIM expression, which is obtained by differentiating an ES cell incorporating targeting vector, is useful in cell biological investigations of AIM in vitro.

For example, if a targeting vector is designed to destroy the function of an exon or promoter by inserting another DNA fragment into the exon portion or promoter region of the AIM gene, the vector can assume, for example, the constitution shown below.

First, to ensure that another DNA fragment is inserted into the exon or promoter portion of the AIM by homologous recombination, the targeting vector need to comprise sequences homologous to the respective target sites (5' arm and 3' arm) upstream of the 5' and downstream of the 3' in the other DNA fragment.

Although the other DNA fragment inserted is not particularly limited, it is possible to select ES cells having a targeting vector integrated in a chromosome thereof with drug resistance or reporter activity as the index, by using a drug resistance gene or a reporter gene. Here, examples of the drug resistance gene and examples of the reporter gene include, but are not limited to, the neomycin phosphotransferase II (nptII) gene, the hygromycin phosphotransferase (hpt) gene and the like, and the β-galactosidase (lacZ) gene, the chloramphenicol acetyltransferase (cat) gene and the like, respectively.

The drug resistance or reporter gene is preferably under the control of an optionally chosen promoter capable of functioning in mammalian cells. For example, virus promoters such as the SV40 early promoter, cytomegalovirus (CMV) long terminal repeat (LTR), Rous sarcoma virus (RSV) LTR, mouse leukemia virus (MoMuLV) LTR, and adenovirus (AdV)-derived early promoter, and promoters for mammalian constitutive protein genes such as the β-actin gene promoter, PGK gene promoter, and transferrin gene promoter and the like can be mentioned. However, if the drug resistance or reporter gene is inserted into the AIM so that it is placed under the control of an endogenous promoter of the AIM, a promoter that controls the transcription of the gene need not be present in the targeting vector.

The targeting vector preferably has a sequence that terminates the transcription of mRNA from the gene (polyadenylation (polyA) signal, also called terminator) downstream of the drug resistance or reporter gene; for example, terminator sequences derived from virus genes, or from various mammal or bird genes, can be used. Preferably, an SV40 terminator and the like are used.

Usually, gene recombination in a mammal occurs mostly non-homologously; the introduced DNA is randomly inserted at an optionally chosen position on the chromosome. Therefore, it is not possible to efficiently select only those clones targeted to the endogenous AIM targeted by homologous recombination by selection based on the detection of the expression of a drug resistance or reporter gene and the like (positive selection); it is necessary to confirm the site of integration by Southern hybridization or PCR for all the clones selected. Hence, provided that, for example, the herpes simplex virus-derived thymidine kinase (HSV-tk) gene, which confers gancyclovir susceptibility, is joined outside the region homologous to the target sequence of the targeting vector, the cells having the vector inserted randomly thereinto cannot grow in a gancyclovir-comprising medium because they have the HSV-tk gene, whereas the cells targeted to the endogenous AIM locus by homologous recombination become resistant to gancyclovir and are selected because they do not have the HSV-tk gene (negative selection). Alternatively, provided that the diphtheria toxin gene, for example, is joined in place of the HSV-tk gene, the cells having the vector inserted randomly thereinto die due to the toxin produced by themselves, so that a homologous recombinant can also be selected in the absence of a drug.

Although any of the calcium phosphate co-precipitation method, electroporation method, lipofection method, retrovirus infection method, aggregation method, microinjection method, gene gun (particle gun) method, DEAE-dextran method and the like can be used for targeting vector introduction into ES cells, the electroporation method is generally chosen because of the ease of treatment of a large number of cells and the like, since gene recombination in a mammal occurs mostly non-homologously so that the frequency of obtainment of homologous recombinants is low, as described above. For the electroporation, ordinary conditions used for transfection into animal cells may be used as is; for example, the electroporation can be performed by trypsinizing ES cells in the logarithmic growth phase to disperse them as single cells, suspending the cells in a medium to obtain a density of $10^6$ to $10^8$ cells/ml, transferring the cells to a cuvette, adding 10 to 100 µg of a targeting vector, and applying an electric pulse of 200 to 600 V/cm.

ES cells having the targeting vector integrated therein can be determined by screening chromosomal DNA separated and extracted from a colony obtained by culturing the single cells on feeder cells, by Southern hybridization or PCR; if a drug resistance gene or a reporter gene is used as the other DNA fragment, it is possible to select a transformant at the cellular stage with the expression thereof as the index. For example, if a vector comprising the nptll gene as the marker gene for positive selection is used, ES cells after transfection treatment are cultured in a medium comprising a neomycin-series antibiotic such as G418, and the resulting resistant colony is selected as a candidate for a transformant. If a vector comprising the HSV-tk gene is used as the marker gene for negative selection, the ES cells are cultured in a medium comprising ganciclovir, and the resulting resistant colony is selected as a candidate for a homologous recombinant. The colonies obtained are transferred to respective culture plates, and trypsinization and medium exchanges are repeated, after which a portion is reserved for cultivation, and the remainder is subjected to PCR or Southern hybridization to confirm the presence of the introduced DNA.

When an ES cell confirmed to have the introduced DNA integrated therein is returned to an embryo derived from a non-human mammal of the same species, the ES cell gets integrated into the ICM of the host embryo to form a chimeric embryo. This is transplanted into a recipient mother (embryo recipient female) and allowed to continue development, whereby a chimeric KO animal is obtained. If the ES cell contributes to the formation of a primordial germ cell that will differentiate into an egg or spermatozoon in the chimeric animal, a germline chimera will be obtained; by mating this, a KO animal having deficiency in the expression of the AIM maintained genetically therein can be prepared.

For preparing a chimeric embryo, there are a method wherein early embryos up to the morula stage are adhered and aggregated together (aggregation chimera method) and a method wherein a cell is micro-injected into a blastocoel cavity of a blastocyst (injection chimera method). Although the latter has traditionally been widely conducted in the preparation of a chimeric embryo using an ES cell, a method wherein an aggregation chimera is created by injecting an ES cell into the zona pellucida of an 8-cell stage embryo, and a method wherein an aggregation chimera is created by co-culturing and aggregating an ES cell mass and an 8-cell stage embryo deprived of the zona pellucida, as a method which does not require a micromanipulator and which can be easily operated, have recently been conducted.

In all cases, a host embryo can be collected from a non-human mammal that can be used as a female for egg collection in transfection into a fertilized egg as below mentioned in the same manner; for example, in the case of a mouse, to make it possible to determine the percent contribution of ES cells to the formation of a chimera mouse by coat color, it is preferable that the host embryo be collected from a mouse of a strain showing a coat color different from that of the strain from which the ES cell is derived. For example, in the case of an ES cell derived from a 129 mouse strain (coat color: agouti), a C57BL/6 mouse (coat color: black) or an ICR mouse (coat color: albino) is used as the female for egg collection; in the case of an ES cell derived from a C57BL/6 or $DBF_1$ mouse (coat color: black) or from a TT2 cell (derived from $F_1$ (coat color: agouti) of C57BL/6 and CBA), an ICR mouse or a BALB/c mouse (coat color: albino) can be used as the female for egg collection.

Because the germline chimera formation capacity depends largely on the combination of an ES cell and a host embryo, it is more preferable that a combination showing a high germline chimera formation capacity be chosen. For example, in the case of a mouse, it is preferable to use a host embryo derived from the C57BL/6 strain and the like for ES cells derived from the 129 strain, and to use a host embryo derived from the BALB/c strain and the like for ES cells derived from the C57BL/6 strain.

It is preferable that the female mouse for egg collection be about 4 to about 6 week-old, and that the male mouse for mating be of the same strain at about 2 to about 8 month-old. Although the mating may be by natural mating, it is preferably performed after administering gonadotropic hormones (follicle-stimulating hormone, then luteinizing hormone) to induce overovulation.

In the case of the blastocyst injection method, a blastocystic embryo (e.g., in the case of a mouse, at about 3.5 days after mating) is collected from the uterus of a female for egg collection (or an early embryo in the morula stage or before, after being collected from the oviduct, may be cultured in a medium (below-mentioned) for embryo culture until the blastocyst stage), and ES cells (about 10 to about 15 cells) having a targeting vector introduced thereinto are injected into a blastocoel cavity of the blastocyst using a micromanipulator, after which the embryos are transplanted into the uterus of a pseudopregnant embryo recipient female non-human mammal. As the embryo recipient female non-human mammal, a non-human mammal that can be used as an embryo recipient female in transfection into a fertilized egg can be used in the same manner.

In the case of the co-culture method, 8-cell stage embryos and morulas (e.g., in the case of a mouse, about 2.5 days after mating) are collected from the oviduct and uterus of a female for egg collection (or an early embryo in the 8-cell stage or before, after being collected from the oviduct, may be cultured in a medium (below-mentioned) for embryo culture until the 8-cell stage or morula stage), and the zona pellucida is lysed in acidic Tyrode's solution, after which an ES cell mass incorporating a targeting vector (number of cells: about 10 to about 15 cells) is placed in a microdrop of a medium for embryo culture overlaid with mineral oil, the above-described 8-cell stage embryo or morula (preferably 2 embryos) is further placed, and they are co-cultured overnight. The morula or blastocyst obtained is transplanted to the uterus of an embryo recipient female non-human mammal as described above.

If the transplanted embryo implants successfully and the embryo recipient female becomes pregnant, chimeric non-human mammal pups will be obtained by natural delivery or caesarean section. Embryo recipient females that have delivered spontaneously are allowed to continue suckling; if the pups are delivered by caesarean section, the pups can be suckled by a separately provided female for suckling (a female non-human mammal with usual mating and delivery).

For the selection of a germline chimera, if the sex of the ES cell has already been determined, a chimera mouse of the same sex as the ES cell first is selected (usually, a male chimera mouse is chosen since a male ES cell is used), and then a chimera mouse showing a high ES cell contribution rate (e.g., 50% or more) is selected on the basis of phenotypes such as coat color. For example, in the case of a chimera mouse obtained from a chimera embryo between a D3 cell, which is a male ES cell derived from a 129 mouse strain, and a host embryo derived from a C57BL/6 mouse, it is preferable that a male mouse showing a high percentage of the agouti coat color be selected. Whether or not the selected chimera non-human mammal is a germline chimera can be determined on the basis of the phenotypes of the $F_1$ animal obtained by crossing with an appropriate strain of the same animal species. For example, in the case of the above-described chimera mouse, agouti is dominant over black; therefore, when the male mouse is crossed with a female C57BL/6 mouse, the coat color of the $F_1$ obtained is agouti if the selected male mouse is a germline chimera.

The thus-obtained germline chimera non-human mammal incorporating a targeting vector (founder) is usually obtained as a heterozygote having the AIM only knocked out in either one of the homologous chromosomes. To obtain a homozygote having the AIM knocked out in both homologous chromosomes, of the $F_1$ animals obtained as described above, siblings of heterozygotes may be crossed. Selection of heterozygotes can be determined by, for example, screening chromosomal DNAs separated and extracted from the tail of an $F_1$ animal by Southern hybridization or PCR. ¼ of the $F_2$ animals obtained will be homozygotes.

In another preferred embodiment with the use of a virus as the targeting vector, a method comprising infecting an ES cell of a non-human mammal with a virus comprising a DNA comprising a marker gene for positive selection inserted between the 5' and 3' arms, and a marker gene for negative selection outside the arms, can be mentioned (see, for example, Proceedings of the National Academy of Sciences, USA (Proc. Natl. Acad. Sci. USA), vol. 99, No. 4, pp. 2140-2145, 2002). For example, when retrovirus or lentivirus is used, cells are sown to an appropriate incubator such as a culture dish, a virus vector is added to the culture broth (if desired, polybrene may be co-present), the cells are cultured for 1 to 2 days, after which, cultivation is continued as described above, and cells having the vector integrated therein are selected.

Regarding specific means for knocking down the AIM, a method comprising introducing a DNA that encodes an antisense RNA or siRNA (including shRNA) of AIM using techniques of preparation of transgenic animals known per se, and allowing it in the subject non-human mammal cell and the like can be mentioned.

A DNA comprising a base sequence complementary to the target region of a desired polynucleotide, i.e., a DNA hybridizable with a desired polynucleotide, can be said to be "antisense" against the desired polynucleotide.

The antisense DNA having a base sequence complementary or substantially complementary to the base sequence of a polynucleotide that encodes AIM or a portion thereof may be any antisense DNA, as long as it comprises a base sequence complementary or substantially complementary to the base sequence of the polynucleotide that encodes AIM or a portion thereof, and having an action to suppress the expression of the polynucleotide.

The base sequence substantially complementary to a polynucleotide that encodes AIM is, for example, a base sequence having a homology of about 70% or more, preferably about 80% or more, more preferably about 90% or more, most preferably about 95% or more, to the base sequence of the complementary strand of the polynucleotide for the overlapping region. Base sequence homology herein can, for example, be calculated using the homology calculation algorithm NCBI BLAST (National Center for Biotechnology Information Basic Local Alignment Search Tool) under the following conditions (expect=10; gap allowed; filtering=ON; match score=1; mismatch score=−3).

Particularly, of the full base sequence of the complementary strand of the polynucleotide that encodes AIM, (a) in the case of an antisense DNA intended to inhibit the translation, an antisense DNA having a homology of about 70% or more, preferably about 80% or more, more preferably about 90% or more, most preferably about 95% or more, to the complementary strand of the base sequence of the portion that encodes the N-terminal part of AIM (e.g., a base sequence in the vicinity of the initiation codon and the like) is suitable, and (b) in the case of an antisense DNA intended to degrade RNA with RNaseH, an antisense DNA having a homology of about 70% or more, preferably about 80% or more, more preferably about 90% or more, most preferably about 95% or more, to the complementary strand of the full base sequence of the polynucleotide that encodes AIM including the intron, is suitable.

Specifically, when the subject non-human mammal is a mouse, an antisense DNA comprising a base sequence complementary or substantially complementary to the base sequence registered under GenBank accession No. AF011428 or a portion thereof, preferably, an antisense DNA comprising a base sequence complementary to the base sequence or a portion thereof, and the like can be mentioned.

An antisense DNA having a base sequence complementary or substantially complementary to the base sequence of a polynucleotide that encodes AIM or a portion thereof (hereinafter, also referred to as "the antisense DNA of the present invention") can be designed and synthesized on the basis of base sequence information on a DNA that encodes cloned or determined AIM. Such antisense DNA is capable of inhibiting the replication or expression of the AIM. Specifically, the antisense DNA of the present invention is capable of hybridizing with an RNA transcribed from the AIM (mRNA or initial transcription product), and capable of inhibiting the synthesis (processing) or function (translation into protein) of mRNA.

The target region of the antisense DNA of the present invention is not particularly limited with respect to the length thereof, as long as the translation into AIM is inhibited as a result of hybridization of the antisense DNA; the target region may be the entire sequence or a partial sequence of the mRNA that encodes the protein, and the length is about 10 bases for the shortest, and the entire sequence of the mRNA or initial transcription product for the longest. Specifically, the 5' end hairpin loop, 5' end 6-base-pair repeats, 5' end untranslated region, translation initiation codon, protein coding region, ORF translation stop codon, 3' end untranslated region, 3' end palindrome region, or 3' end hairpin loop of the AIM may be chosen as a preferable target region of the antisense DNA, but any other region in the AIM gene may also be chosen as the target. For example, the intron portion of the gene may also be the target region.

Furthermore, the antisense DNA of the present invention may be one that not only hybridizes with the mRNA or initial transcription product of AIM to inhibit the translation into protein, but also is capable of binding to the AIM being a double-stranded DNA to form a triple strand (triplex) and hence to inhibit the transcription to RNA. Alternatively, the antisense DNA of the present invention may be one that forms a DNA:RNA hybrid to induce the degradation by RNaseH.

A DNA that encodes a ribozyme capable of specifically cleaving the mRNA that encodes AIM or the initial transcription product within the coding region (including the intron portion in the case of the initial transcription product) can also be encompassed in the antisense DNA of the present invention. One of the most versatile ribozymes is a self-splicing RNA found in infectious RNAs such as viroid and virusoid, and the hammerhead type, the hairpin type and the like are known. The hammerhead type exhibits enzyme activity with about 40 bases in length, and it is possible to specifically cleave the target mRNA by making several bases at both ends flanking to the hammerhead structure portion (about 10 bases in total) a sequence complementary to the desired cleavage site of the mRNA. Because this type of ribozyme has only RNA as the substrate, it offers an additional advantage of non-attack of genomic DNA. Provided that the AIM mRNA assumes a double-stranded structure per se, the target sequence can be made to be single-stranded by using a hybrid ribozyme prepared by joining an RNA motif derived from a viral nucleic acid that can bind specifically to RNA helicase [Proc. Natl. Acad. Sci. USA, 98(10): 5572-5577 (2001)]. Furthermore, the ribozyme may be a hybrid ribozyme prepared by further joining a sequence modified from the tRNA to promote the translocation of the transcription product to cytoplasm [Nucleic Acids Res., 29(13): 2780-2788 (2001)].

Herein, a double-stranded RNA consisting of an oligo-RNA homologous to a partial sequence (including the intron portion in the case of the initial transcription product) in the coding region of the mRNA or initial transcription product of AIM and a strand complementary thereto, what is called a single-chain interfering RNA (siRNA), can also be used to prepare the KD animal of the present invention. It had been known that so-called RNA interference (RNAi), which is a phenomenon that when siRNA is introduced into cells, an mRNA homologous to the RNA is degraded, occurs in nematodes, insects, plants and the like; since this phenomenon was confirmed to also occur in animal cells [Nature, 411(6836): 494-498 (2001)], siRNA has been widely utilized as an alternative technique to ribozymes. siRNA can be designed as appropriate on the basis of base sequence information of the mRNA being the target using commercially available software (e.g., RNAi Designer; Invitrogen).

The antisense oligo-DNA and ribozyme of the present invention can be prepared by determining the target sequence for the mRNA or initial transcription product on the basis of a cDNA sequence or genomic DNA sequence of AIM, and synthesizing a sequence complementary thereto using a commercially available DNA/RNA synthesizer (Applied Biosystems, Beckman, and the like). By inserting the synthesized antisense oligo-DNA or ribozyme downstream of the promoter in the expression vector, via an appropriate linker (adapter) sequence used as required, a DNA expression vector that encodes the antisense oligo-RNA or ribozyme can be prepared. Examples of expression vectors that can be used preferably here include plasmids amplified with *Escherichia coli, Bacillus subtilis*, or yeast, bacteriophages such as λ phage, retroviruses such as Moloney leukemia virus, animal or insect viruses such as lentivirus, adeno-associated virus, vaccinia virus and baculovirus, and the like. In particular, plasmids (preferably plasmids from *Escherichia coli, Bacillus subtilis*, or yeast, particularly plasmids from *Escherichia coli*) and animal viruses (preferably retrovirus, lentivirus) are preferable. Examples of promoters include virus promoter such as the SV40 early promoter, cytomegalovirus (CMV) long terminal repeat (LTR), Rous sarcoma virus (RSV) LTR, mouse leukemia virus (MoMuLV) LTR, and adenovirus (AdV) derived early promoter, and promoters for mammalian constitutive protein genes such as the β-actin gene promoter, PGK gene promoter, and transferrin gene promoter and the like.

A DNA expression vector that encodes a longer antisense RNA (e.g., full-length complementary strand of AIM mRNA and the like) can be prepared by inserting an AIM cDNA, cloned by a conventional method, in the reverse direction, via an appropriate linker (adapter) sequence used as required, downstream of the promoter in the expression vector.

Meanwhile, a DNA that encodes siRNA can be prepared by separately synthesizing a DNA that encodes a sense strand and a DNA that encodes an antisense strand, and inserting them into an appropriate expression vector. As the siRNA expression vector, one having a Pol III system promoter such as U6 or H1 can be used. In this case, in the animal cell incorporating the vector, the sense strand and the antisense strand are transcribed and annealed to form siRNA. shRNA can be prepared by inserting a unit comprising a sense strand and an antisense strand separated by a length base allowing the formation of an appropriate loop structure (e.g., about 15 to 25 bases) into an appropriate expression vector. As the shRNA expression vector, one having a Pol III system promoter such as U6 or H1 can be used. In this case, the shRNA transcribed in the animal cell incorporating the expression vector forms a loop by itself, and is then processed by an endogenous enzyme dicer and the like to form mature siRNA. Alternatively, it is also possible to achieve knockdown by RNAi by expressing a microRNA (miRNA) comprising the siRNA sequence being the target using a Pol II system promoter. In this case, by a promoter showing tissue-specific expression, tissue-specific knockdown is also possible.

For introducing an expression vector comprising a DNA that encodes an antisense RNA, siRNA, shRNA, or miRNA of AIM into a cell, a method known per se is used as appropriate according to the target cell. For example, for introduction into an early embryo such as a fertilized egg, the microinjection method is used. For introduction into an ES cell, the calcium phosphate co-precipitation method, electroporation method, lipofection method, retrovirus infection method, aggregation method, microinjection method, particle gun method, DEAE-dextran method and the like can be used. Alternatively, when retrovirus, lentivirus and the like are used as the vector, it is sometimes possible to achieve transfection conveniently by adding the virus to an early embryo or an ES cell, and culturing the embryo or cell for 1 to 2 days to infect the cells with the virus. Regeneration of individuals from an ES cell (establishment of founder), passage (preparation of homozygotes) and the like can be performed as described above with respect to the KO animal of the present invention.

In a preferred embodiment, the expression vector comprising a DNA that encodes an antisense RNA, siRNA, shRNA, or miRNA of AIM is introduced into an early embryo (fertilized egg) of a non-human mammal being the subject by microinjection.

DNA microinjection into the fertilized egg can be performed by a conventional method using a commonly known device such as a micromanipulator. Briefly, the fertilized egg placed in a microdrop of a medium for embryo culture is aspirated and immobilized using a holding pipette, and a DNA solution is injected directly into the male or female pronucleus, preferably into the male pronucleus, using an injection pipette. The introduced DNA is used preferably after being highly purified using CsCl density gradient ultracentrifugation or an anion exchange resin column and the like. It is also preferable that the introduced DNA be linearized in advance by cutting the vector portion using a restriction endonuclease.

After introducing the DNA, the fertilized egg is cultured in a medium for embryo culture in 5% gaseous carbon dioxide/95% atmosphere by the microdrop culture method and the like until the 1-cell stage to blastocyst stage, after which it is transplanted to the oviduct or uterus of a female non-human mammal for embryo reception rendered to be pseudopregnant. The female non-human mammal for embryo reception may be any one of the same species as the animal from which the early embryo to be transplanted is derived; for example, when a mouse early embryo is transplanted, a female ICR mouse (preferably about 8 to about 10 weeks of age) and the like are preferably used. A known method of rendering a female non-human mammal for embryo reception pseudopregnant is, for example, a method comprising mating the female with a vasectomized (vasoligated) male non-human mammal of the same species (e.g., in the case of a mouse, with a male ICR mouse (preferably about 2 months or more of age)), and selecting a female confirmed to have a vaginal plug.

The female for embryo reception used may be one that has ovulated spontaneously, or one receiving luteinizing hormone releasing hormone (generally abbreviated as LHRH) or an analogue thereof administered prior to mating with a vasectomized (vasoligated) male, to induce fertility. Examples of the LHRH analogue include [3,5-DiI-Tyr$^5$]-LH-RH, [Gln$^8$]-LH-RH, [D-Ala$^6$]-LH-RH, [des-Gly$^{10}$]-LH-RH, [D-His(Bzl)$^6$]-LH-RH and Ethylamides thereof and the like. The amount of LHRH or an analogue thereof administered, and the time of mating with a male non-human mammal after the administration vary depending on the species of the non-human mammal. For example, when the non-human mammal is a mouse (preferably an ICR mouse and the like), it is usually preferable that the female mouse be mated with a male mouse about 4 days after administration of LHRH or an analogue thereof; the amount of LHRH or an analogue thereof administered is usually about 10 to 60 μg/individual, preferably about 40 μg/individual.

Usually, if the early embryo to be transplanted is in the morula stage or after, the embryo is transplanted to the uterus of a female for embryo reception; if the early embryo is in a stage before the morula stage (e.g., 1-cell stage to 8-cell stage embryo), the embryo is transplanted to the oviduct. The female for embryo reception is used as appropriate after elapse of a given number of days after becoming pseudopregnant depending on the developmental stage of the embryo to be transplanted. For example, in the case of a mouse, a female mouse at about 0.5 days after becoming pseudopregnant is preferable for the transplantation of a 2-cell stage embryo, and a female mouse at about 2.5 days after becoming pseudopregnant is preferable for the transplantation of a blastocystic embryo. After the female for embryo reception is anesthetized (preferably, Avertin, Nembutal and the like are used), an incision is made, the ovary is pulled out, and early embryos (about 5 to about 10 embryos) in suspension in a medium for embryo culture are injected into the vicinity of the abdominal osteum of the uterine tube or the uterine tube junction of the uterine horn using a pipette for embryo transplantation.

When the transplanted embryo implants successfully and the embryo recipient female becomes pregnant, non-human mammal pups will be obtained by spontaneous delivery or caesarian section. Embryo recipient females that have delivered spontaneously are allowed to continue suckling; when the pups are delivered by caesarian section, the pups can be suckled by a separately provided female for suckling (e.g., in the case of the mouse, a female mouse with usual mating and delivery (preferably a female ICR mouse and the like)).

Transfer of the DNA that encodes an antisense RNA, siRNA, shRNA, or miRNA of AIM in the fertilized egg cell stage is secured so that the introduced DNA will be present in all of the germline cells and somatic cells of the subject non-human mammal. Whether or not the introduced DNA is integrated in chromosomal DNA can be determined by, for example, screening chromosomal DNAs separated and extracted from the tail of the pup, by Southern hybridization or PCR. The presence of the expression vector in the germline cells of the offspring non-human mammal ($F_0$) obtained as described above means that the expression vector is present in all of the germline cells and somatic cells of all animals in the subsequent generation ($F_1$).

Usually, $F_0$ animals are obtained as heterozygotes having the introduced DNA in either of the homologous chromosomes. Different $F_0$ individuals have the introduced DNA inserted randomly on different chromosomes unless the insertion is by homologous recombination. To obtain a homozygote having the expression vector in both of the homologous chromosomes, an $F_0$ animal and a non-transgenic animal are crossed to prepare an $F_1$ animal, and heterozygous siblings thereof having the introduced DNA in either of the homologous chromosomes may be crossed. If the introduced DNA is integrated only at one gene locus, ¼ of the $F_2$ animals obtained will be homozygotes.

In another preferred embodiment with the use of a virus as the vector, as with the above-described case of KO animals, a method comprising infecting an early embryo or ES cell of a non-human mammal with a virus comprising a DNA that encodes an antisense RNA, siRNA, shRNA, or miRNA of AIM can be mentioned. When a fertilized egg is used as the cell, it is preferable that the zone pallucida be removed prior to infection. After cultivation for 1 to 2 days following infection with the virus vector, the fertilized egg is transplanted to the oviduct or uterus of a female non-human mammal for embryo reception rendered to be pseudopregnant as described above in the case of an early embryo, or the fertilized egg is continued to be cultured with the addition of a selection drug as described above in the case of an ES cell, and a cell incorporating the vector is selected.

Furthermore, as described in the Proceedings of the National Academy of Sciences, USA (Proc. Natl. Acad. Sci. USA), vol. 98, pp. 13090-13095, 2001, a spermatogonium collected from a male non-human mammal is infected with a virus vector during co-cultivation with STO feeder cells, after which the spermatogonium is injected into the seminiferous tube of a male infertile non-human mammal, and the male infertile non-human mammal is mated with a female non-human mammal, whereby pups that are hetero-Tg (+/−) for a DNA that encodes an antisense RNA, siRNA, shRNA, or miRNA of AIM can be obtained efficiently.

The non-human mammal deficient in the expression of the AIM gene of the present invention, which is described in Miyazaki T. et al. (J. Exp. Med., 189, 413-422, 1999), or obtained by the above-mentioned method, has the following characteristics under high fat diet loading conditions:
(1) liver weight increases,
(2) fatty liver is promoted,
(3) liver cancer is developed, and/or
(4) inflammation response is suppressed in the liver.
In addition, the non-human mammal deficient in AIM expression of the present invention characteristically shows promoted liver fibrosis under high fat diet loading conditions, like the wild-type animals. These phenotypes have not been reported at least in conventionally publicly known AIM KO mice.
Particularly, changes from fatty liver to liver fibrosis to liver cancer are similar to the pathology of NASH, which is a new finding.

(1) That the liver weight increases means that the liver weight and/or liver weight/body weight (%) become(s) significantly different in the non-human mammal deficient in AIM expression of the present invention as compared to wild-type animals by loading with a high fat diet. In the below-mentioned Examples, significant differences were found in the AIM knockout mouse from week 6 of the high fat diet loading, as compared to wild-type mouse.

(2) That the fatty liver is promoted means that accumulation of fat is observed in the liver of the non-human mammal deficient in AIM expression of the present invention in an early stage, as compared to wild-type animals, by loading with a high fat diet. The accumulation of fat in the liver can also be confirmed by, for example, staining a hepatic tissue section with oil red O. Alternatively, it can also be confirmed by measuring the amount of neutral fat in the liver tissue. In the below-mentioned Examples, significant differences were found in the AIM knockout mouse from week 6 of the high fat diet loading, as compared to wild-type mouse.

(3) That liver cancer is developed means that the onset of liver cancer is observed in the non-human mammal deficient in AIM expression of the present invention by loading with a high fat diet. Liver cancer can be confirmed, for example, by staining a hepatic tissue section with anti-AFP (α-fetoprotein), measuring the AFP expression level in a hepatic tissue, or measuring the blood AFP concentration. In the below-mentioned Examples, liver cancer could scarcely be confirmed in wild-type mouse even after one year from high fat diet loading, but liver cancer was found in all AIM knockout mice one year from high fat diet loading.

(4) That an inflammation response is suppressed in the liver means that an inflammation response is suppressed in the AIM expression deficient non-human mammal of the present invention as compared to wild-type animals, even when they were loaded with a high fat diet. Inflammation response can be confirmed by the expression of, for example, F4/80 (macrophage marker), TNFα, IL-6 or IL-1β. In the below-mentioned Examples, inflammation in the liver was significantly suppressed in AIM knockout mouse from week 12 of high fat diet loading, as compared to wild-type mouse.

That liver fibrosis is promoted means that liver fibrosis is observed in the non-human mammal deficient in AIM expression of the present invention by loading with a high fat diet, like wild-type animals. Liver fibrosis can be confirmed by, for example, staining a hepatic tissue section with sirius red. While it is known that collagen synthesis due to hepatic stellate cell is involved in liver fibrosis, it can also be confirmed by the expression of αSMA, which is a marker of hepatic stellate cell. It can also be confirmed by the expression of TGEβ1, Collagen 4A1 in the liver. In the below-mentioned Examples, liver fibrosis was observed in the wild-type mouse and AIM knockout mouse from week 20 of high fat diet loading. Also, high expression of αSMA was observed in the wild-type mouse and AIM knockout mouse from week 20 of high fat diet loading. TGFβ1 tended to show an increase in the expression level, in proportion to the length of the high fat diet loading period. However, a significant difference was not observed in the level of fibrosis, and the expression level of αSMA and TGFβ1, between the wild-type mouse and the AIM knockout mouse.

These findings indicate that a non-human mammal deficient in AIM expression placed under high fat diet loading conditions is useful as an animal model of hepatic diseases, and can be further used for screening for a prophylactic or therapeutic drug for hepatic diseases. Specifically, the screening method of the present invention comprises the following steps:
(1) a step of administering, under high fat diet loading conditions, a test substance to a non-human mammal deficient in AIM expression,
(2) a step of observing any one or more items of the following properties of the non-human mammal deficient in AIM expression, which is administered with the test substance:
(i) liver weight,
(ii) liver fat amount,
(iii) liver fiber,
(iv) liver cancer, and
(v) inflammation response in liver, and
(3) a step of selecting a test substance that improves the aforementioned properties by comparison to non-administration of the test substance.

A high fat diet used for loading a non-human mammal deficient in AIM expression in the screening method of the present invention is not particularly limited as long as the lipid content is high. It generally has a lipid content of not less than 20%, preferably not less than 30%, more preferably not less than 40%. The period of loading a non-human mammal deficient in AIM expression with a high fat diet is at least until the aforementioned properties can be confirmed. The loading period is not less than 6 weeks, more preferably not less than 12 weeks, further preferably not less than 20 weeks.

As a test substance to be administered to a non-human mammal deficient in AIM expression, proteins, peptides, antibodies, non-peptide compounds, synthetic compounds, fermentation products, cell extracts, plant extracts, animal tissue extracts, plasma and the like can be used. The timing of administration of the test substance may be before the start of high fat diet loading or simultaneously with the start thereof, or after observation of the aforementioned property following high fat diet loading of the non-human mammal deficient in AIM expression. The administration method may be oral or parenteral. For oral administration, it can be administered by mixing with a feed or drinking water. As parenteral administration, intraperitoneal administration, administration by intravenous injection, subcutaneous injection, intradermal injection, muscular injection, drip injection and the like, rectal administration of suppository and the like can be mentioned. The administration may include a single administration or multiple administrations.

The property of a non-human mammal deficient in AIM expression, which is administered with a test substance is observed after administration of the test substance, generally 4 weeks or later, preferably 6 weeks or later. As for the liver weight, it can be observed by measuring the weight of the liver isolated from the aforementioned mammal and/or liver weight/body weight (%). As for the liver fat, it can be observed by staining a hepatic tissue section of the liver isolated above with oil red O, and converting the staining level thereof into numerical values, or measuring the amount of neutral fats in a hepatic tissue. As for the liver fiber, it can be observed by staining a hepatic tissue section of the liver isolated above with sirius red, and converting the staining level thereof into numerical values. Alternatively, as for the liver fiber, it can also be confirmed by converting the expression level of αSMA (α-smooth muscle actin), TGFβ1 or Collagen 4A1 in the liver isolated above into numerical values. As for the liver cancer, it can be observed by staining a hepatic tissue section of the liver isolated above with anti-AFP (α-fetoprotein), and converting the staining level thereof into numerical values, converting the expression level of AFP in the liver isolated above into numerical values, or measuring the blood AFP concentration. As for the inflammation response in the liver, it can be confirmed by converting the expression level of F4/80, TNFα, IL-6 or IL-1β in the liver isolated above into a numerical value.

The observation results of the aforementioned property obtained as mentioned above are compared with those in the case of non-administration of the test substance. Alternatively, a correlational figure of the presence or absence of a hepatic disease and the aforementioned properties is drawn in advance and the obtained observation results of the aforementioned properties may be compared with the correlational figure. Comparison is preferably performed based on the presence or absence of a significant difference.

When the obtained observation results of the aforementioned properties are improved than non-administration of the test substance, the test substance can be selected as an agent for the prophylaxis or treatment of hepatic diseases. Here, being improved means that (i) the liver weight is lower than non-administration of the test substance, (ii) the liver fat amount (level of oil red O staining, or amount of neutral fats) is lower than non-administration of the test substance, (iii) the level of liver fibrosis (level of sirius red staining, expression of αSMA, TGFβ1, Collagen4A1) is lower than non-administration of the test substance, (iv) AFP expression is lower than non-administration of the test substance, of (v) expression of F4/80, TNFα, IL-6, IL-1β is higher than non-administration of the test substance.

When the test substance selected in the above is used as an agent for the prophylaxis or treatment of hepatic diseases, it can formulated in the same manner as in the AIMs of the present invention, and administered by a similar administration route and at a similar dose. The hepatic diseases to be the target of the prophylactic or therapeutic agent may be similar to those mentioned above.

In addition, since a non-human mammal deficient in AIM expression under high fat diet loading conditions is useful as an animal model of hepatic diseases, the mammal can be used for the evaluation method of a prophylactic or therapeutic drug for hepatic diseases. Accordingly, the present invention also provides a method of evaluating a prophylactic or therapeutic effect of a prophylactic or therapeutic agent for a hepatic disease, comprising using an animal obtained by loading a non-human mammal deficient in AIM expression with a high fat diet. Specifically, the evaluation method of the present invention comprises the following steps:

(1) a step of administering, under high fat diet loading conditions, a prophylactic or therapeutic agent for a hepatic disease to a non-human mammal deficient in AIM expression, (2) a step of observing any one or more items of the following properties of the non-human mammal deficient in AIM expression, which is administered with the prophylactic or therapeutic agent for a hepatic disease:
(i) liver weight,
(ii) liver fat amount,
(iii) liver fiber,
(iv) liver cancer,
(v) inflammation response in liver, (3) a step of evaluating an effect of the prophylactic or therapeutic agent for a hepatic disease by comparison of the aforementioned properties to those of non-administration of the prophylactic or therapeutic agent for a hepatic disease.

The prophylactic or therapeutic agent for a hepatic disease to be administered to a non-human mammal deficient in AIM expression in the evaluation method of the present invention may be a known prophylactic or therapeutic agent for a hepatic disease. Examples thereof include, but are not limited to, insulin sensitizers (e.g., thiazolidine derivatives such as rosiglitazone, pioglitazone and the like, and the like, biguanides such as metformin, buformin and the like); antioxidants (e.g., vitamin E, vitamin C, betaine, EPL (Polyenephosphatidylcholine) etc.); liver supporting agents (e.g., ursodeoxycholic acid (UDCA) etc.); anti-hyperlipidemia agents (e.g., fibrate drugs, probucol, statin drugs etc.); depressors (e.g., angiotensin II receptor antagonists etc.); glycyrrhizin preparation; Chinese herbal medicines (e.g., shosaikoto etc.); anticancer agents and the like. The administration period, administration method, administration frequency and the like of a prophylactic or therapeutic agent for a hepatic disease may be the same as those in the aforementioned screening method.

An observation method of the property to be observed by the evaluation method of the present invention may be performed according to the aforementioned description of the screening method. When the observation results of the aforementioned properties obtained by the evaluation method are improved by a larger degree than non-administration of a prophylactic or therapeutic agent for a hepatic disease, the test substance can be evaluated as having a higher prophylactic or therapeutic effect as an agent for the prophylaxis or treatment of hepatic diseases. As used herein, being improved means the same as above.

In the below-mentioned Examples of the present invention, the AIM concentration of the sera of NASH patients was confirmed to be lower than that of non-NASH patients. Particularly, the AIM concentration of the sera of NASH patients who progressed to liver cancer was confirmed to be still lower than that of NASH patients who did not progress to liver cancer. From the above, it is suggested that hepatic diseases can be diagnosed by measuring the blood AIM concentration of test subjects. Specifically, the diagnosis method of the present invention comprises the following steps:

(1) a step of measuring the AIM concentration of a sample of a test subject, (2) a step of comparing the aforementioned AIM concentration of the sample of the test subject with the AIM concentration of a sample of a healthy human, (3) a step of judging that the test subject has a hepatic disease or has a high possibility of developing a hepatic disease, when the aforementioned AIM concentration of the sample of the test subject is lower than the AIM concentration of the sample of the healthy human.

While the test subject to whom the diagnosis method of the present invention is applicable is not particularly limited, for example, a test subject having a risk of developing a hepatic disease or suspected to have developed a hepatic disease can be mentioned. While such test subject is not limited, for example, test subjects having symptoms of obesity, diabetes, hypertension, arteriosclerosis, hyperlipidemia and the like can be mentioned. As the healthy human, those who have not been clinically diagnosed to have a hepatic disease, for example, one free of the aforementioned symptoms can be mentioned.

A sample to be used for the diagnosis method of the present invention is not particularly limited as long as it is collected from the above-mentioned test subject, and comprises an AIM gene product (e.g., RNA, protein, lysis product thereof and the like) to be the measurement target. Examples thereof include body fluids such as blood, plasma, serum, lymph fluid, urine, sweat, saliva, synovial fluid and the like or a fraction thereof, and cells contained therein, particularly macrophage and the like.

The AIM concentration of a sample collected from a test subject can be measured by preparing an RNA (e.g., total RNA, mRNA) fraction from macrophage, and measuring a transcription product of AIM gene contained in the fraction. While an RNA fraction can be prepared by using a known method such as guanidine-CsCl ultracentrifugation method, AGPC method and the like, highly pure total RNA can be prepared rapidly and conveniently from a trace amount of macrophage by using a commercially available RNA extraction kit (e.g., RNeasy Mini Kit; manufactured by QIAGEN etc.). Examples of the method for detecting a transcription product of AIM gene in an RNA fraction include a method using hybridization (Northern blot, dot blot, DNA chip analysis etc.), a method using PCR (RT-PCR, competitive PCR, real-time PCR etc.) and the like. Quantitative PCR methods such as competitive PCR, real-time PCR and the like are preferable since variation in the expression of AIM gene can be detected rapidly, conveniently and highly quantitatively from a trace amount of macrophage.

When Northern blot or dot blot hybridization is employed, a transcription product of AIM gene can be measured by using a nucleic acid (probe) capable of hybridization with a transcription product of the gene. Examples of such nucleic acid include a nucleic acid capable of hybridization with a nucleic acid comprising a base sequence shown by a transcription product of AIM gene (e.g., base sequence shown in SEQ ID NO: 1) under highly stringent conditions. The highly stringent conditions are the aforementioned conditions and the like.

The nucleic acid to be used as a probe may be double-stranded or single-stranded. In the case of a double-stranded nucleic acid, it may be a double-stranded DNA, a double-stranded RNA, or a DNA:RNA hybrid. In the case of a single strand, an antisense strand can be used. While the length of the nucleic acid is not particularly limited as long as it can specifically hybridize with a target nucleic acid, for example, it is not less than about 15 bases, preferably not less than about 30 bases. The nucleic acid is preferably labeled with a label to enable detection and quantification of the target nucleic acid. As the labeling agent, for example, radioisotopes, enzymes, fluorescent substances, luminescent substances and the like are used. As the radioisotope, for example, $[^{32}P]$, $[^{3}H]$, $[^{14}C]$ and the like are used. As the enzymes described above, stable enzymes with a high specific activity are preferred; for example, beta-galactosidase, beta-glucosidase, alkaline phosphatase, peroxidase, malate dehydrogenase and the like are used. As the fluorescent substance, for example, fluorescamine, fluorescein isothiocyanate and the like are used. As the luminescent substances, for example, luminol, luminol derivatives, luciferin, lucigenin and the like are used. Furthermore, biotin-(strept) avidin can also be used for binding a probe and a label.

When Northern hybridization is employed, an RNA fraction prepared as mentioned above is separated by gel electrophoresis, transcribed onto a membrane of nitrocellulose, nylon, polyvinylidenedifluoride and the like, hybridized under the above-mentioned highly stringent conditions in a hybridization buffer comprising a labeling probe prepared as mentioned above, and the amount of the label bound to the membrane is measured for each band by a suitable method, whereby the expression level of AIM gene can be measured. Also, in the case of dot blot, the expression level of AIM gene can be measured by subjecting a membrane spotted with RNA fractions to a hybridization reaction in the same manner and measuring the amount of the label of the spot.

In another preferable embodiment, a quantitative PCR method is used as a method for measuring AIM concentration. Examples of the quantitative PCR include competitive PCR, real-time PCR and the like.

A set of oligonucleotides used as primers in PCR is not particularly limited as long as they can each specifically hybridize with a sense strand (coding strand) and an antisense strand (noncoding strand) of a transcription product of the AIM gene, and can amplify the DNA fragment sandwiched by them. For example, a set of oligoDNAs each having a length of about 15-about 100 bases, preferably about 15-about 50 bases, and designed to amplify about 100 bp-1 kbp DNA fragments can be mentioned. More specifically, as a set of oligonucleotides used as primers, a nucleic acid capable of hybridizing with a nucleic acid (antisense strand) comprising the base sequence complementary to the aforementioned base sequence under highly stringent conditions can be mentioned. As used herein, the highly stringent conditions are as defined above.

In competitive RT-PCR, the amount of desired DNA is determined by allowing a known amount of another template nucleic acid that can be amplified by a set of primers capable of amplifying the desired DNA, as the competitor, to coexist in the reaction liquid to cause a competitive amplification reaction, and comparing the amounts of the amplification products. Therefore, when competitive RT-PCR is used, in addition to the above-mentioned primer set, a known amount of a competitor nucleic acid that can be amplified with the primer set, and can be distinguished from an amplification product of the target nucleic acid (i.e., transcription product of AIM gene) after the amplification (e.g., different amplification size, different migration pattern of restriction enzyme treated fragment and the like) is used. Since amplification occurs competitively as the target nucleic acid and the competitor nucleic acid struggle for the primers, the quantitative ratio of the amplification product reflects the quantitative ratio of the original template. The competitor nucleic acid may be DNA or RNA. In the case of DNA, a cDNA is synthesized from an RNA fraction prepared as mentioned above by a reverse transcription reaction, and PCR may be performed in the co-presence of the above-mentioned primer set and competitor. In the case of RNA, competitor is added to an RNA fraction and a reverse transcription reaction is performed, and the above-mentioned primer set is added and PCR is performed. In the latter case, the absolute amount of the original mRNA can be estimated because the reverse transcription reaction efficiency is also taken into consideration.

In real-time PCR, the amplification amount is monitored in real-time using a fluorescent reagent, and an apparatus integrally comprising a thermal cycler and a spectrofluorophotometer is necessary. Such apparatus is commercially available. There are several methods depending on the fluorescent reagent to be used and, for example, intercalator method, TaqMan™ probe method, Molecular Beacon method and the like can be mentioned. In any case, cDNA is synthesized by reverse transcription reaction from an RNA fraction prepared as mentioned above, and the above-mentioned primer set and a fluorescence reagent (probe), for example, reagents (intercalator) emitting fluorescence by binding to double stranded DNA such as SYBR Green I, ethidium bromide and the like, nucleic acids usable as the above-mentioned probes (the nucleic acid hybridizes to the target nucleic acid within amplification region), wherein the both ends are respectively modified with a fluorescent substance (e.g., FAM, HEX, TET, FITC etc.) and a quenching substance (e.g., TAMRA, DABCYL etc.) (TaqMan™-probe or Molecular Beacon probe) and the like, are each added to PCR reaction system. Since intercalator binds to a synthesized double stranded DNA and emits fluorescence upon irradiation of excitation light, the amount of an amplification product can be monitored by measuring the intensity of fluorescence, based on which the amount of original template cDNA can be assumed. The TaqMan™ probe is an oligonucleotide capable of hybridizing to an amplification region of the target nucleic acid, which has both ends modified by a fluorescent substance and a quenching substance, respectively. It hybridizes to a target nucleic acid during annealing but is prohibited from emitting fluorescence by the presence of the quenching substance, and emits fluorescence when decomposed by the exonuclease activity of DNA polymerase during elongation, which releases the fluorescent substance. Accordingly, by measuring fluorescence intensity, the amount of the amplification product can be monitored, based on which the amount of original template cDNA can be assumed. The Molecular Beacon probe is an oligonucleotide capable of hybridizing to an amplification region of a target nucleic acid and having a hairpin type secondary structure, which has both ends modified by a fluorescent substance and a quenching substance, respectively. When it has a hairpin structure, it does not emit fluorescence due to the presence of a quenching substance, and emits fluorescence when the distance between the fluorescent substance and the quenching substance grows upon hybridization to the target nucleic acid during annealing. Therefore, the amount of the amplification product can be monitored by measuring the fluorescence intensity, based on which the amount of original template cDNA can be assumed. Since real-time RT-PCR permits real-time monitoring of the amplification amount of PCR, it does not require electrophoresis and can analyze the expression of AIM gene more rapidly.

In another embodiment, the AIM concentration of a sample collected from a test subject can be measured by preparing protein fractions from the sample and detecting AIM contained in the fraction. Detection of AIM can be performed by an immunological measurement method (e.g., ELISA, FIA, RIA, Western blot etc.) using an antibody to AIM. Alternatively, detection of AIM can also be performed by a mass spectrometry method such as MALDI-TOFMS and the like.

An antibody to AIM can be obtained according to a generally-used technique for producing a polyclonal antibody or monoclonal antibody, and using a protein comprising an amino acid sequence the same or substantially the same as the amino acid sequence shown in SEQ ID NO: 2, or a partial amino acid sequence thereof as an immunization antigen.

In applying these individual immunological measurement methods to the diagnosis method of the present invention, it is unnecessary to set special conditions, procedures and the like. Making ordinary technical considerations for those skilled in the art to the ordinary conditions and procedures in each method, a measurement system for AIM can be constructed. For details of these general technical means, compendia, books and the like can be referred to. For example, Hiroshi Irie, ed., "Radioimmunoassay" (Kodansha Ltd., published in 1974), Hiroshi Irie, ed., "Sequel to the Radioimmunoassay" (Kodansha Ltd., published in 1979), Eiji Ishikawa et al., ed., "Enzyme Immunoassay" (Igakushoin, published in 1978), Eiji Ishikawa et al., ed., "Enzyme Immunoassay" (2nd ed.) (Igakushoin, published in 1982), Eiji Ishikawa et al., ed., "Enzyme Immunoassay" (3rd ed.) (Igakushoin, published in 1987), Methods in ENZYMOLOGY, Vol. 70 (Immunochemical Techniques (Part A)), ibidem, Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibidem, Vol. 92 (Immunochemical Techniques (Part E: Monoclonal Antibodies and General Immunoassay Methods)), ibidem, Vol. 121 (Immunochemical Techniques (Part I: Hybridoma Technology and Monoclonal Antibodies)) (all published by Academic Press Publishing) and the like.

As mentioned above, the blood concentration of AIM of the present invention decreases in patients with hepatic diseases. Therefore, when AIM concentration is measured as mentioned above and the results show a decreased concentration as compared to healthy human, the test subject can be judged to have developed a hepatic disease or have a high possibility of developing a hepatic disease. Alternatively, a correlational figure of the presence or absence of a hepatic disease and AIM concentration is drawn in advance and the obtained observation results may be compared with the correlational figure. Comparison is preferably performed based on the presence or absence of a significant difference.

The sequence identification numbers in the sequence listing herein show the following sequences.
[SEQ ID NO: 1]
Shows the base sequence of human AIM.
[SEQ ID NO: 2]
Shows the amino acid sequence of human AIM.
[SEQ ID NO: 3]
Shows the base sequence of a sense primer for F4/80.
[SEQ ID NO: 4]
Shows the base sequence of an antisense primer for F4/80.
[SEQ ID NO: 5]
Shows the base sequence of a sense primer for TNFα.
[SEQ ID NO: 6]
Shows the base sequence of an antisense primer for TNFα.
[SEQ ID NO: 7]
Shows the base sequence of a sense primer for IL-6.
[SEQ ID NO: 8]
Shows the base sequence of an antisense primer for IL-6.
[SEQ ID NO: 9]
Shows the base sequence of a sense primer for IL-1β.
[SEQ ID NO: 10]
Shows the base sequence of an antisense primer for IL-1β.

[SEQ ID NO: 11]
Shows the base sequence of a sense primer for αSMA.
[SEQ ID NO: 12]
Shows the base sequence of an antisense primer for αSMA.
[SEQ ID NO: 13]
Shows the base sequence of a sense primer for TGFβ1.
[SEQ ID NO: 14]
Shows the base sequence of an antisense primer for TGFβ1.
[SEQ ID NO: 15]
Shows the base sequence of a sense primer for AFP.
[SEQ ID NO: 16]
Shows the base sequence of an antisense primer for AFP.
[SEQ ID NO: 17]
Shows the base sequence of a sense primer for GAPDH.
[SEQ ID NO: 18]
Shows the base sequence of an antisense primer for GAPDH.

EXAMPLES

The present invention is hereinafter described more specifically by means of the following Examples and Reference Examples, to which the invention is not limited.

Example 1: Promotion of Fatty Liver by Loading AIM Knockout Mouse with High Fat Diet (HFD)

Liver weight, weight of liver relative to body weight, weight of neutral fat in liver, and accumulation of liver fat by hematoxylin-eosin tissue staining were studied by loading AIM knockout mouse and WT mouse with a high fat diet (HFD). As a result, loading of WT mouse with HFD did not result in clear difference in the liver weight/body weight up to week 20, but loading of AIM knockout mouse with HFD resulted in a significant increase in liver weight/body weight as compared to WT from week 6 (FIG. 1A). In addition, the results of the weight of neutral fat in the liver show that loading of AIM knockout mouse with HFD resulted in the accumulation of fat in the liver from week 6, and it has been clarified that fatty liver was promoted as compared to WT (FIG. 1B).

Example 2: Progression of Liver Fibrosis (Cirrhosis) by Loading AIM Knockout Mouse with High Fat Diet (HFD)

Figure 2:
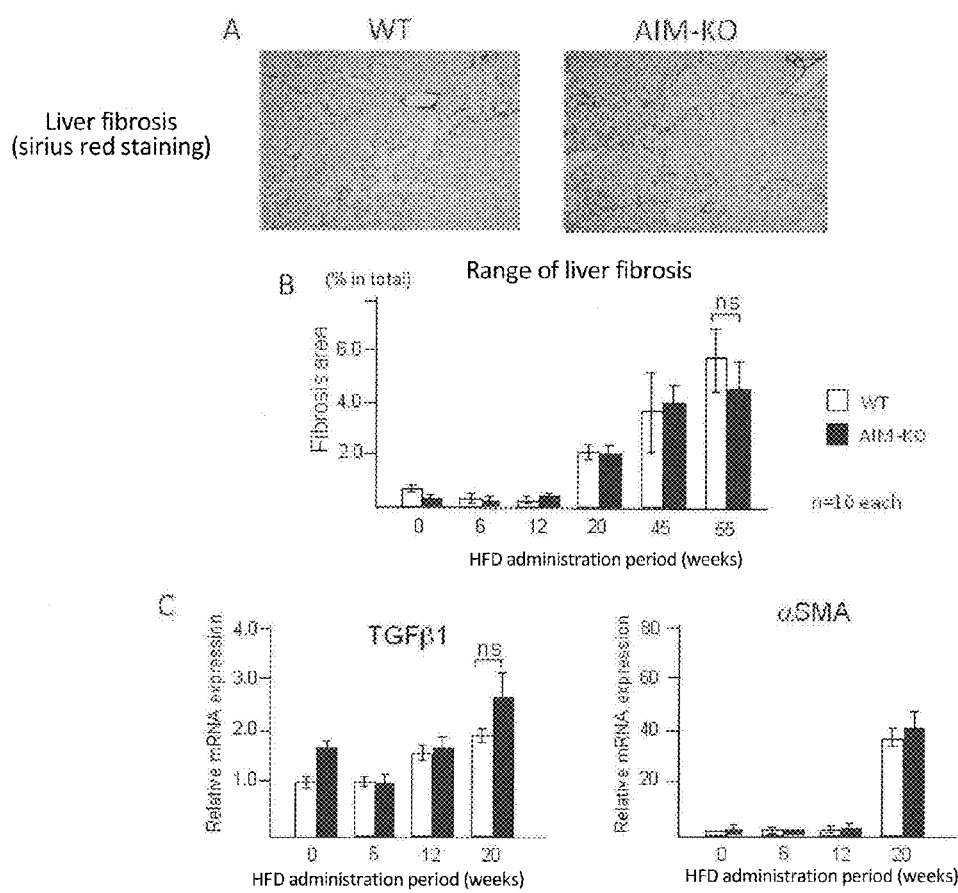
FIG. 2 A: images of hepatic tissue sections of AIM KO mice and WT mice on week 20 after loading with a high fat diet. B: graph showing the ratio of fibrosis in hepatic tissue sections of AIM KO mice and WT mice loaded with a high fat diet for 0, 6, 12, 20, 45, 55 weeks. C: graphs showing relative mRNA expression levels of TGFβ1 and αSMA in the liver of AIM KO mice and WT mice loaded with a high fat diet.

Wild-type mouse (male, 10 mice, 12-week-old) and AIM knockout mouse (male, 10 mice, 12-week-old) were loaded with a high fat diet (HFD), 0, 6, 12, 20, 45, 55 weeks later, the liver was fixed with formalin, pieces were stained with sirius red, and the stained fibrosis area (FIG. 2A) was quantified by NIH-J image. Each mouse was analyzed with three discontinuous pieces and mean (ratio of fibrosis to whole piece) is shown (FIG. 2B). As a result, fibrosis area increases as the HFD loading period becomes longer, but a significant difference was not found between the wild-type mouse and the AIM knockout mouse. Moreover, RNA was extracted from a part of hepatic tissue before fixing and the mRNA expression level of αSMA and TGFβ, which are representative genes involved in liver fibrosis, was analyzed by quantitative RT-PCR (FIG. 2C). Since cancer is frequently developed in AIM knockout mouse at 45, 55 weeks after high fat diet (HFD) loading and accurate expression level of normal liver area is difficult to analyze, the RNA analysis was performed only in mice loaded for 0, 6, 12, 20 weeks. As a result, while the mRNA expression level of αSMA and TGFβ increased with HFD loading, a significant difference was not found between them.

Example 3: Onset of Hepatocyte Cancer by Loading AIM Knockout Mouse with High Fat Diet (HFD)

Figure 3:
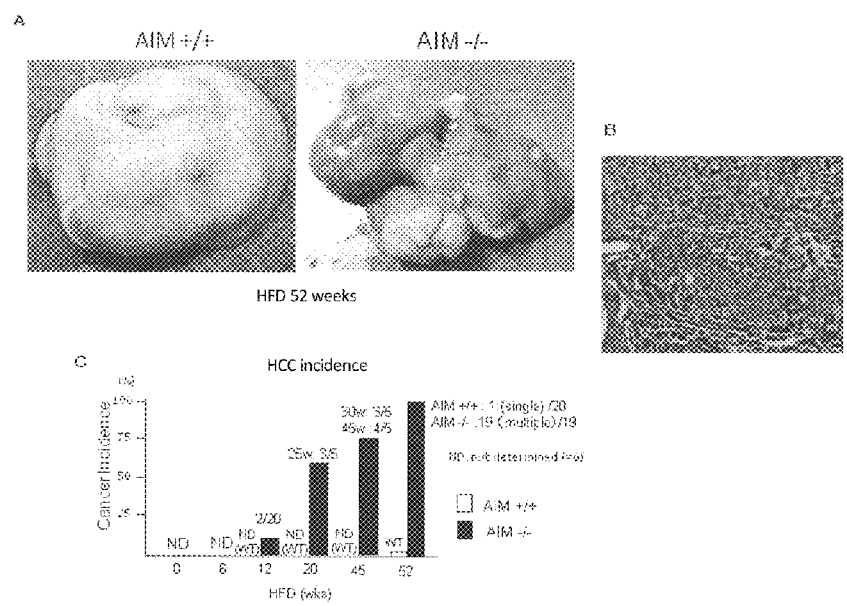
FIG. 3 shows A: photographic images of the liver isolated from AIM KO mice (indicated as AIM−/−) and WT mice (indicated as AIM+/+) loaded with a high fat diet for 52 weeks; B: hematoxylin-eosin-stained image of hepatic tissue section of AIM KO mice loaded with a high fat diet for 52 weeks; C: graph showing the onset frequency of well-differentiated hepatocyte cancer (HCC) in hepatic tissue sections of AIM KO mice and WT mice loaded with a high fat diet for 0, 6, 12, 20, 45, 52 weeks.
Figure 4:
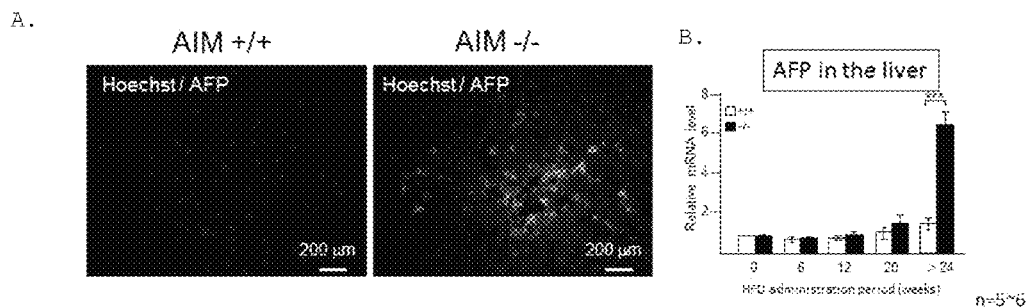
FIG. 4 shows A: anti-AFP antibody-stained images of hepatic tissue sections, and B: a graph showing the relative expression levels of AFP in the liver of AIM KO mice and WT mice loaded with a high fat diet.

When WT mouse was loaded with HFD for 52 weeks, fatty liver was observed but hepatocyte cancer was not developed mostly. However, hepatocyte cancer was observed in all AIM knockout mice, and almost all the observed tumor was high differentiation type hepatocyte cancer (HCC) (FIG. 3A, B, C). Hepatocyte cancer was confirmed in the liver of AIM knockout mouse by Hoechst/AFP staining (FIG. 4), and promoted expression of AFP in the liver was also confirmed.

Figure 5:
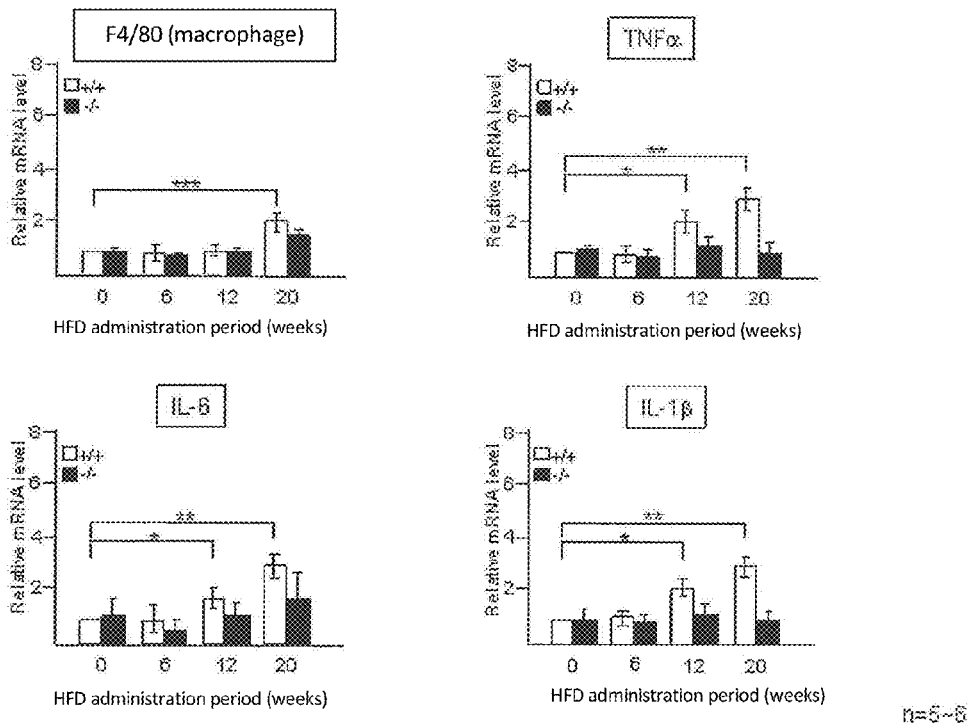
FIG. 5 presents graphs showing the relative expression levels of F4/80 (macrophage), TNFα, IL-6, IL-1β in the liver of AIM KO mice and WT mice loaded with a high fat diet. mean±SEM, *; $P<0.05$, ; $P<0.01$, *; $P<0.001$.

Example 4: Inflammation Response of AIM Knockout Mouse by High Fat Diet (HFD) Loading Inflammation response in the liver was suppressed by loading AIM knockout mouse with a high fat diet (HFD) (FIG. 5). When WT mouse was loaded with HFD, promoted inflammation responses such as accumulation of macrophage in the liver, and promoted expression of TNFα, IL-6, IL-1β were observed at weeks 12-20. In contrast, these inflammation responses were suppressed in AIM knockout mouse as compared to WT (FIG. 5).

Example 5: Stabilizing of Blood AIM by IgM

Figure 6:
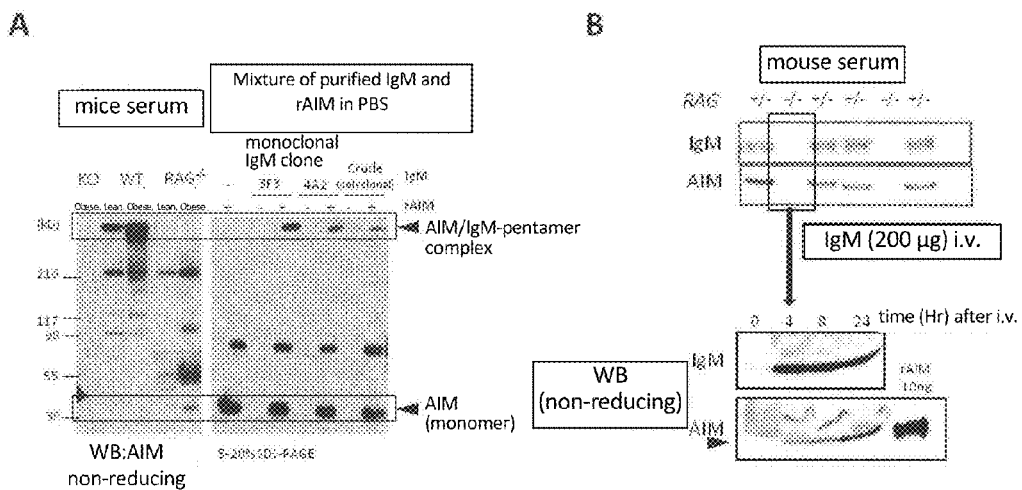
FIG. 6 shows A: Western blot image of AIM present the sera of AIM KO mice, WT mice and RAG KO mice, and Western blot image of AIM bound in vitro to monoclonal or polyclonal IgM, and B: Western blot image of AIM present in the serum of RAG KO mice intravenously injected with IgM.
Figure 7:
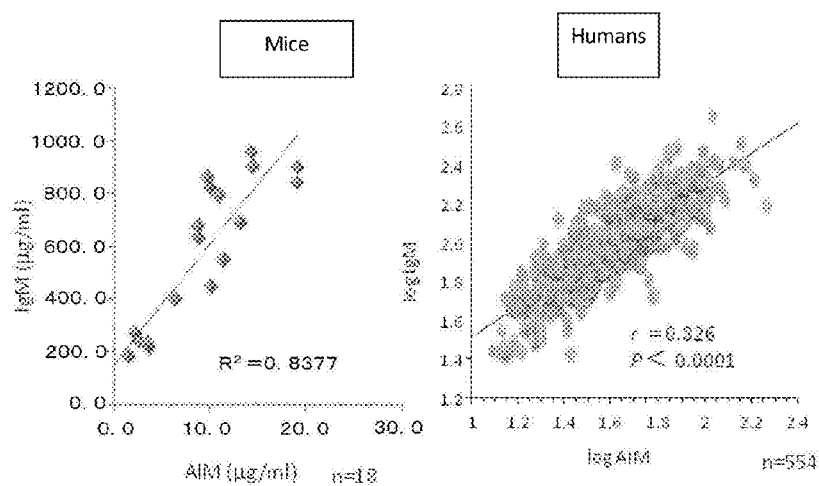
FIG. 7 shows graphs indicating the correlation between AIM and IgM levels in the sera of mice and humans.

Serum AIM of RAG (Recombination-activating gene) KO mouse to that lacks IgM in blood due to the absence of B lymphocyte was analyzed by Western blot. As compared to WT, RAG KO mouse showed an extremely low level of AIM in serum, and AIM-IgM complex was not detected (FIG. 6A). Thus, binding of AIM and IgM was examined in vitro to confirm binding of AIM and IgM (FIG. 6A). Furthermore, 200 µg of IgM was intravenously administered to RAG KO mouse. As a result, blood AIM increased (FIG. 6B). Furthermore, the AIM concentration and IgM concentration of mouse and human sera were measured by an ELISA method. As a result, it was clarified that the blood AIM concentration and IgM concentration are correlated also in human, as in mouse (FIG. 7). From the above, AIM was suggested to form a complex with IgM and is stabilized in blood.

Example 6: Fatty Liver Suppressive Effect of AIM in Vitro

Figure 8:
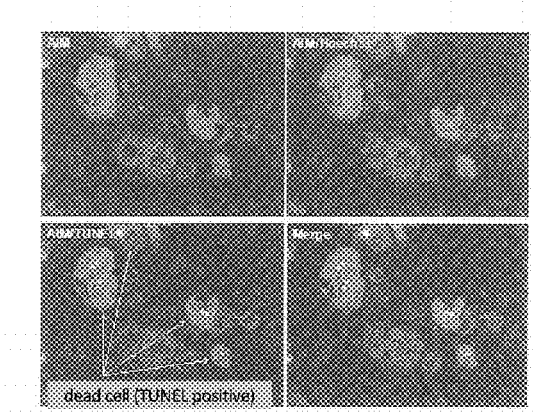
FIG. 8 shows A: anti-AIM antibody-stained images, and B: Western blot images of mouse primary cultured hepatocytes incubated with AIM.
Figure 8:
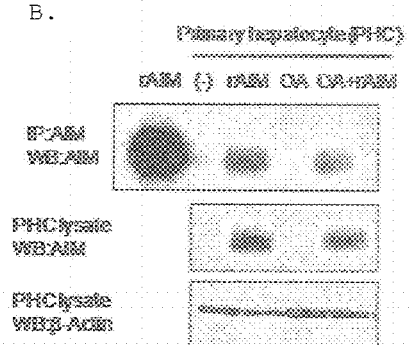
Figure 9:
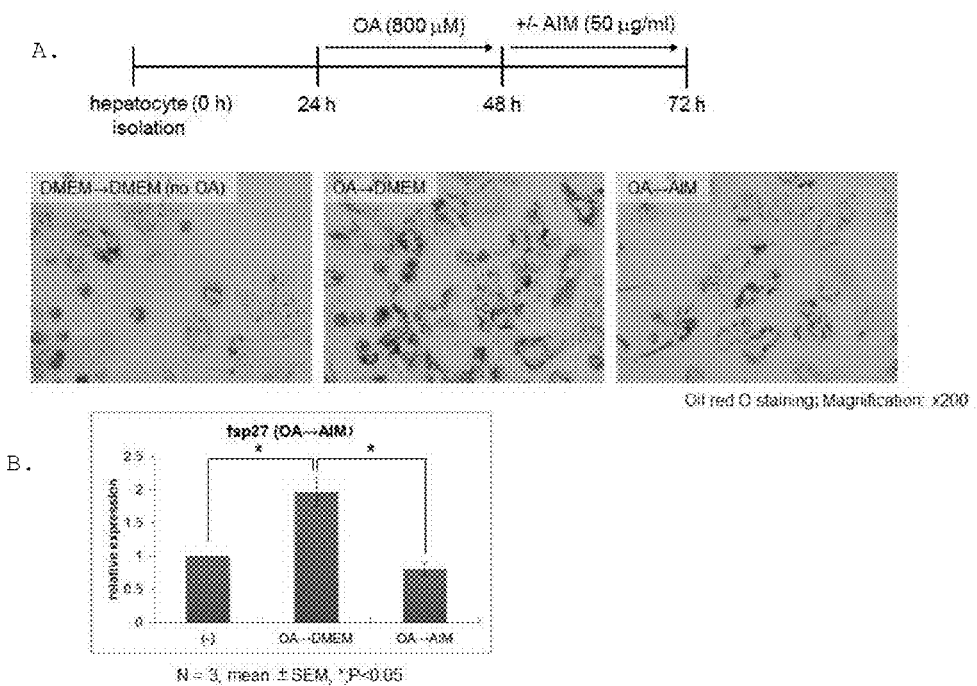
FIG. 9 shows images of mouse primary cultured hepatocytes incubated with or without AIM after preculture with oleic acid, and a graph showing the relative expression level of FSP27 in the cell.

The action of AIM on hepatocyte in vitro was studied. Mouse primary cultured hepatocytes were reacted with AIM for 5 hr, and the cells were stained with anti-AIM antibody and subjected to Western blot. As a result, it was confirmed that AIM was uptaken by the cells (FIG. 8). Furthermore, 800 µM oleic acid (OA) was added to mouse primary cultured hepatocytes, and the cells were cultured for 24 hr to generate fatty liver, and further cultured for 24 hr with or without addition of AIM. The level of fatty liver was measured from staining and mRNA expression level of FSP27 (Fat-Specific protein 27). By AIM nonaddition (OA→DMEM), the level of staining and fsp27 expression level increased as compared to OA nonaddition, and the level of fatty liver was confirmed (FIG. 9). On the other hand, by AIM addition (OA→AIM), the level of staining and fsp27 expression level did not increase (FIG. 9), and a fatty liver improving effect of AIM was confirmed.

Figure 10:
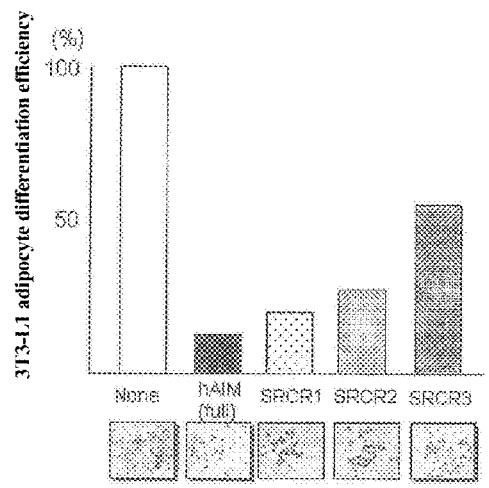
FIG. 10 is a graph showing the adipocyte differentiation suppressive effect of AIM or each SRCR domain protein in 3T3-L1 preadipocytes.

Example 7: Suppression of Differentiation of Preadipocyte into Adipocyte by SRCR Domain Recombinant human SRCR domain (SRCR1, SRCR2, SRCR3) proteins were obtained by expressing each human SRCR domain added with HA (hemagglutinin) tag in HEK293T cells, and purifying same by an anti-HA antibody column. 3T3-L1 preadipocytes were cultured in the presence of 1 µg/mL insulin, 1 µM dexamethasone (DEX), 0.5 mM isobutylmethylxanthine (IBMX) for 48 hr to induce differentiation into adipocytes, and the differentiation suppressive actions of SRCR domain and AIM were studied. AIM added was human full-length AIM (hAIM), and the aforementioned 3 kinds of SRCR domain proteins were used at 20 µg/ml. Differentiation into adipocyte was quantified based on the level of oil red O staining without addition as 100%. An adipocyte differentiation suppressive action, which is the same as that of AIM, was found in all SRCR domains (FIG. 10).

Example 8: Measurement of Serum AIM Concentration of NASH Patients

Figure 11:
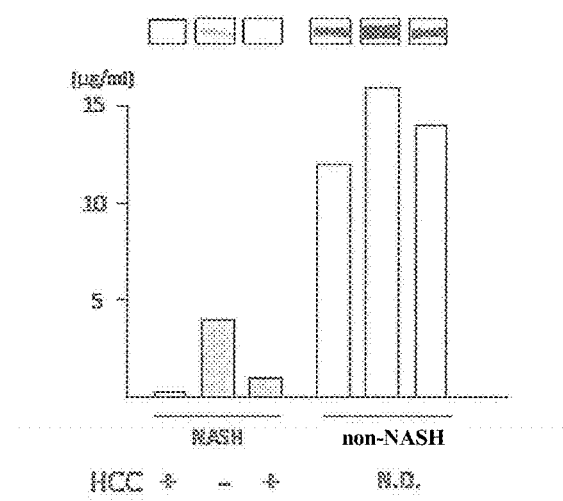
FIG. 11 is a graph showing the AIM concentration of serum in NASH patients and non-NASH patients.

Serum AIM concentration was measured in 3 cases of NASH patients (2 cases progressed to hepatocyte cancer) and 3 cases of non-NASH patients. The measurement was performed by Western blot using an anti-AIM antibody, and the intensity of the signal was quantified. NASH patients showed a decreased serum AIM concentration as compared to non-NASH patients (FIG. 11). In addition, NASH patients progressed to hepatocyte cancer showed a more decreased serum AIM concentration (FIG. 11).

Reference Example: Effect of AIM Administration on AIM Knockout Mouse Loaded with High Fat Diet (HFD)

8-week-old AIM KO mouse is bred while loading with a high fat diet (HFD). AIM or vehicle is administered every day from weeks 2-3 of HFD loading and before accumulation of fat in the liver is observed. When the liver is stained with oil red O at 4-6 weeks after the administration, fat accumulation is observed in the vehicle administration group, whereas it is not found in the AIM administration group. Therefore, it is known that AIM is useful for the prophylaxis of fatty liver. Also, 8-week-old AIM KO mouse is bred while loading with a high fat diet (HFD). AIM or vehicle is administered every day from weeks 6-8 of HFD loading and before accumulation of fat in the liver is observed. When the liver is stained with oil red O at 4-8 weeks after the administration, fat accumulation increases in the vehicle administration group as compared to that before administration, whereas fat accumulation decreases in the AIM administration group as compared to that before administration. Therefore, it is known that AIM is useful for the improvement or treatment of fatty liver. In addition, similar results are also obtained by using, instead of AIM, a drug capable of agonistically controlling the function of AIM (including a partial peptide of AIM having AIM activity) or a drug that induces the expression of AIM. Similarly, a prophylactic, improving or therapeutic effect of AIM on cirrhosis and liver cancer can also be confirmed by administering AIM at the time point when liver fibrosis and liver cancer are developed.

Example 9: Effect of AIM Administration on AIM Knockout Mouse Loaded with High Fat Diet (HFD)

Figure 12:
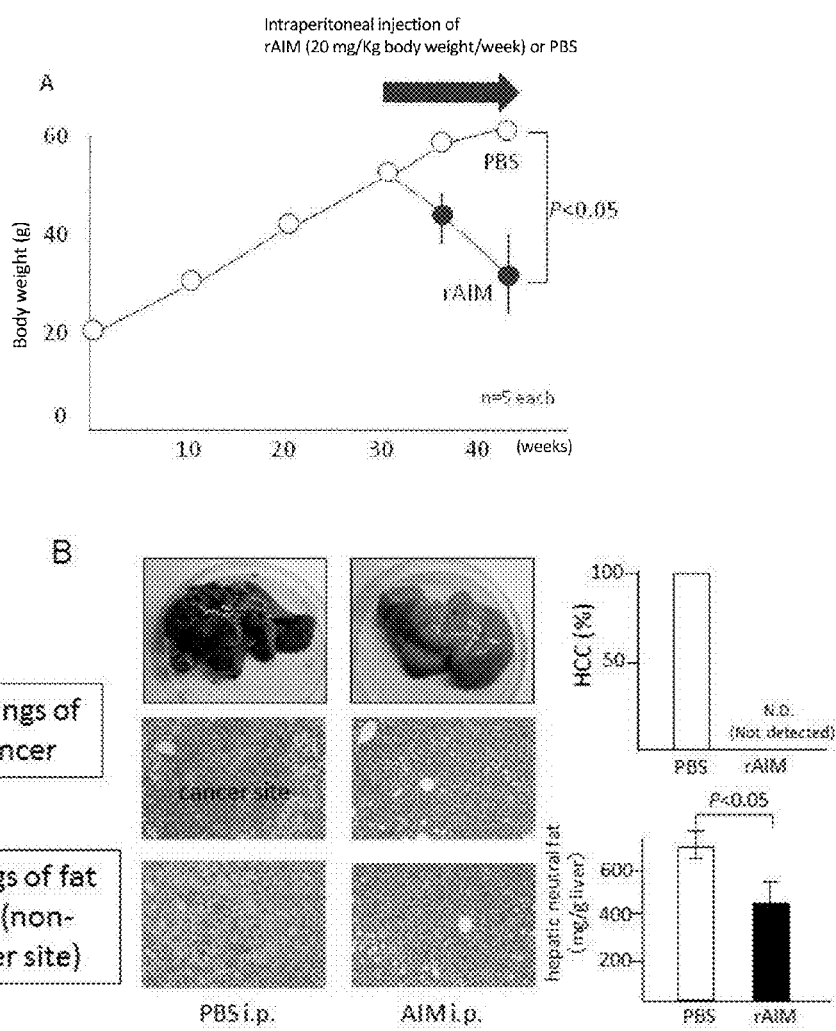
FIG. 12 presents A: a graph showing the changes in the body weight in AIM KO mice fed a high fat diet with rAIM or PBS, and B: macroscopic images of liver, hematoxylin-eosin stained image of hepatic tissue section (cancer site, non-cancer site), a graph showing the cancer onset rate, and a graph showing the amount of hepatic neutral fat in AIM KO mice fed a high fat diet with rAIM or PBS.

AIM knockout mice (male 10 mice, 12-week-old) were loaded with a high fat diet (HFD) for 43 weeks, and recombinant AIM (rAIM) (20 mg/Kg(body weight); 5 mice) or PBS (5 mice) was administered by intraperitoneal injection once per week from week 30 to week 43. On week 43 of HFD, the mice were slaughtered, the isolated liver was fixed with formalin, and hepatic tissue pieces were prepared. The obtained hepatic tissue pieces were stained with hematoxylin-eosin, and the state of cancer and the state of fatty liver were analyzed. The hepatic tissue pieces were prepared at 10 non-continuous pieces for each mouse, and the presence or absence of cancer, size and number were analyzed. In addition, the liver (non-cancer part) was partly removed before fixing and the content of neutral fats was measured. As a result, the body weight of the rAIM administration group significantly decreased. On the other hand, the body weight of the PBS administration group increased (FIG. 12A). A clear cancer part was not found in the rAIM administration group. In contrast, all mice had plural cancer nodules in the PBS administration group. Also, multiple liver cancer was found histologically. Macroscopic photographs and hematoxylin-eosin stained images are shown (FIG. 12B). As for fatty liver, histologically clear improvement was observed in the rAIM administration group. In addition, the neutral fat content of the liver (non-cancer part) significantly decreased as compared to that of the PBS administration group (FIG. 12B).

INDUSTRIAL APPLICABILITY

The present invention can provide a prophylactic or therapeutic agent for a hepatic disease, comprising AIM as an active ingredient. In addition, the hepatic disease model mouse of the present invention contributes to the elucidation of the onset mechanism of hepatic diseases and, according to the screening method using the hepatic disease model mouse, a substance effective to the prophylaxis or treatment for hepatic diseases can be searched. In addition, using the hepatic disease model mouse of the present invention, effects of a known prophylactic or therapeutic agent for a hepatic disease can be evaluated. Furthermore, the present invention can provide a method for diagnosis of a hepatic disease.

This application is based on patent application No. 2012-103958 filed in Japan (filing date: Apr. 27, 2012), the contents of which are incorporated in full herein.

The invention claimed is:

1. A method of prophylaxis of hepatocellular carcinoma in a non-alcoholic steatohepatitis (NASH) patient, comprising administering to the NASH patient an effective amount of an Apoptosis Inhibitor of Macrophage (AIM) consisting of the amino acid sequence represented by SEQ ID NO:2.

2. A method of treatment of hepatocellular carcinoma progressed from non-alcoholic steatohepatitis (NASH) in a patient in need thereof, comprising administering to the patient an effective amount of an Apoptosis Inhibitor of Macrophage (AIM) consisting of the amino acid sequence represented by SEQ ID NO:2.

3. The method according to claim 1, wherein the effective amount of the AIM is from 0.01 to 20 mg/kg body weight.

4. The method according to claim 2, wherein the effective amount of the AIM is from 0.01 to 20 mg/kg body weight.

5. The method according to claim 1, wherein the AIM is administered in a pharmaceutical composition further comprising a carrier or excipient.

6. The method according to claim 5, wherein the pharmaceutical composition is formulated for injection.

7. The method according to claim 2, wherein the AIM is administered in a pharmaceutical composition further comprising a carrier or excipient.

8. The method according to claim 7, wherein the pharmaceutical composition is formulated for injection.

9. The method according to claim 1, wherein the AIM is administered by injection.

10. The method according to claim 2, wherein the AIM is administered by injection.

* * * * *